(12) United States Patent
Yoon et al.

(10) Patent No.: US 10,195,166 B2
(45) Date of Patent: Feb. 5, 2019

(54) METHODS FOR TREATING HEPATITIS C VIRUS INFECTIOUS DISEASE

(71) Applicant: THE CATHOLIC UNIVERSITY OF KOREA INDUSTRY-ACADEMIC COOPERATION FOUNDATION, Seoul (KR)

(72) Inventors: Seung Kew Yoon, Seoul (KR); Jung Hee Kim, Seoul (KR); Won Hee Hur, Seoul (KR); Mi La Cho, Seoul (KR); Jung Eun Choi, Gyeonggi-do (KR); Eun Byul Lee, Gyeonggi-do (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 2 days.

(21) Appl. No.: 15/032,717

(22) PCT Filed: Oct. 28, 2014

(86) PCT No.: PCT/KR2014/010200
§ 371 (c)(1),
(2) Date: Apr. 28, 2016

(87) PCT Pub. No.: WO2015/065020
PCT Pub. Date: May 7, 2015

(65) Prior Publication Data
US 2016/0271229 A1  Sep. 22, 2016

(30) Foreign Application Priority Data

Oct. 29, 2013 (KR) .................. 10-2013-0129139
Oct. 23, 2014 (KR) .................. 10-2014-0144534

(51) Int. Cl.
| A61K 38/17 | (2006.01) |
| A61K 31/155 | (2006.01) |
| A61K 31/196 | (2006.01) |
| C12N 15/113 | (2010.01) |
| A61K 31/7072 | (2006.01) |
| A61K 31/7105 | (2006.01) |
| A61K 38/00 | (2006.01) |
| A61K 48/00 | (2006.01) |

(52) U.S. Cl.
CPC .......... *A61K 31/155* (2013.01); *A61K 31/196* (2013.01); *A61K 31/7072* (2013.01); *A61K 31/7105* (2013.01); *A61K 38/1709* (2013.01); *C12N 15/1137* (2013.01); *C12N 2310/14* (2013.01); *C12Y 106/05003* (2013.01); *C12Y 203/0102* (2013.01)

(58) Field of Classification Search
CPC ............ A61K 38/00; A61K 38/1709; A61K 2300/00; A61K 48/00
See application file for complete search history.

(56) References Cited

U.S. PATENT DOCUMENTS

| 4,224,179 A | 9/1980 | Schneider |
| 4,231,877 A | 11/1980 | Yamauchi et al. |
| 4,235,871 A | 11/1980 | Papahadjopoulos et al. |
| 4,247,411 A | 1/1981 | Vanlerberghe et al. |
| 4,394,448 A | 7/1983 | Szoka, Jr. et al. |
| 4,673,567 A | 6/1987 | Jizomoto |
| 4,753,788 A | 6/1988 | Gamble |
| 4,814,270 A | 3/1989 | Piran |
| 4,897,355 A | 1/1990 | Eppstein et al. |
| 5,366,737 A | 11/1994 | Eppstein et al. |
| 5,622,712 A | 4/1997 | Eppstein et al. |
| 2008/0194456 A1* | 8/2008 | Podolsky ............. C12Q 1/6883 514/1.1 |

FOREIGN PATENT DOCUMENTS

KR          101215670 B1    12/2012

OTHER PUBLICATIONS

Lufei, C. et al. GRIM-19, a death-regulatory gene product, suppresses Stat3 activity via functional interaction. EMBO J., 2003, vol. 22, No. 6, p. 1325-1335.*
Chung, C., et al., "Specific Inhibition of Stat3 Signal Transduction by PIAS3," Science, Dec. 5, 1997, vol. 278, pp. 1803-1806.
Li, F. et al., Downregulation of GRIM-19 is associated with hyperactivation of p-STAT3 in hepatocellular carcinoma, Medical Oncology, vol. 29, Issue 5, Apr. 1, 2012, pp. 3046-3054.
Machida, K. et al., "c-Jun Mediates Hepatitis C Virus Hepatocarcinogenesis Through Signal Transducer and Activator of Transcription 3 and Nitric Oxide-Dependent Impairment of Oxidative DNA Repair," Hepatology, vol. 52, No. 2, Aug. 2010, pp. 480-492.
Merritield, R., "Solid Phase Peptide Synthesis. I. The Synthesis of a Tetrapeptide," Journal of the American Chemical Society, vol. 85, Issue 14, Jul. 20, 1963, pp. 2149-2154.
Zhang, J. et al., "The cell death regulator GRIM-19 is an inhibitor of signal transducer and activator of transcription 3," Proc. Natl. Acad. Sci. USA, vol. 100, No. 16, Aug. 5, 2003, pp. 9342-9347.
International Search Report dated Dec. 18, 2014 in corresponding International Application No. PCT/KR2014/010200, 8 pages.

* cited by examiner

*Primary Examiner* — Robert S Landsman
*Assistant Examiner* — Bruce D. Hissong
(74) *Attorney, Agent, or Firm* — Carter, Deluca, Farrell & Schmidt, LLP

(57) ABSTRACT

The present invention relates to a pharmaceutical composition for preventing or treating hepatitis C virus (HCV) infectious disease. More particularly, the present invention relates to a pharmaceutical composition for preventing or treating HCV infectious disease or an antiviral composition for HCV, containing at least one selected from the group consisting of: GRIM19 protein or a fragment thereof; and a gene encoding the protein or a fragment of the protein.

15 Claims, 17 Drawing Sheets
Specification includes a Sequence Listing.

HCV-infected patients

HBV-infected patients

METHODS FOR TREATING HEPATITIS C VIRUS INFECTIOUS DISEASE

CROSS REFERENCE TO RELATED APPLICATIONS

This application is a national stage application of International Application No. PCT/KR2014/010200, filed on Oct. 28, 2014, which claims the benefit of and priority to Korean Patent Application No. 10-2013-0129139, filed on Oct. 29, 2013, and Korean Patent Application No. 10-2014-0144534, filed Oct. 23, 2014, the entire contents of each of which are hereby incorporated by reference herein in their entireties.

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "6758US_Sequence Listing" created on Apr. 26, 2016 and is 14.8 KB in size. The sequence listing contained in this .txt file is part of the specification and is hereby incorporated by reference herein in its entirety.

TECHNICAL FIELD

The present invention relates to a pharmaceutical composition for preventing or treating a hepatitis C virus (HCV) infectious disease. More particularly, the present invention relates to a pharmaceutical composition for preventing or treating a hepatitis C virus infectious disease or an antiviral composition against hepatitis C virus, comprising at least one selected from the group consisting of Genes-associated with Reinoid-Interferon induced Morality 19 (GRIM19) protein or a fragment thereof, and a gene encoding the protein or the fragment thereof.

BACKGROUND ART

Hepatitis C virus (HCV) has infected about 180 million people worldwide. HCV infected patients suffer from acute hepatitis, part of whom is completely cured, but most of whom (50 to 80%) develop chronic hepatitis. It is known that about 20% of chronic hepatitis patients develop liver cirrhosis or liver cancer.

At present, as there is no commercialized vaccine against HCV, the medical approach to prevention thereof is impossible. As the standard-of-care treatment for HCV, a combination therapy of PEG-IFN-α and ribavirin, a nucleoside analogue, is used. However, there may be side effects including flu like symptoms (fever, fatigue, muscular pain, headache, chill, etc.), anemia, neutropenia, thrombocytopenia, increase in serum ALT, neuropsychiatric disorders, thyroid dysfunction, respiratory diseases (interstitial pneumonia, etc.), ocular disorders (retinal hemorrhage, loss of color sense, etc.), skin diseases (erythema, rash, etc.), hair loss, etc.

Also, the standard-of-care treatment for HCV exhibits limited effects depending on HCV genotypes. A sustained virological response (SVR; absence of detectable HCV in serum for 6 months after stopping therapy) reached about 80% for genotypes 2 and 3, whereas a SVR reached less than 50% for genotypes 1 and 4, which means that the likelihood of recurrence is high.

Recently, in order to overcome the limited effect of the combination therapy of PEGylated interferon and ribavirin, drugs of direct-acting antivirals (DAA) have been developed. Telaprevir and boceprevir have been approved and used as HCV NS3-NS4A protease inhibitors. However, these drugs are also known to show limited effect for genotype 1b, and drug resistance is a matter of concern.

Therefore, it is urgent to develop anti-HCV drugs which can be used to patients on whom the standard-of-care treatment for HCV does not work and are applicable with no limitation to genotypes.

Meanwhile, GRIM19, a cell death-associated gene, is currently known as a partner interacting with STAT3 through yeast-2-hybrid screening (Zhang J, Yang J, Roy S K, Tininini S, Hu J, Bromberg J F. et al. Proc Natl Acad Sci USA. 2003; 100:9342-9347). GRIM19 is also known to inhibit STAT3-mediated transcription without inhibiting phosphorylation of tyrosine and serine residues or blocking its binding to DNA (Chung C D, Liao J, Liu B, Rao X, Jay P, Berta P. et al. Science. 1997; 278:1803-1805). However, there is no report on GRIM19 in relation with hepatitis C virus.

Under such background, the present inventors confirmed that the expression of GRIM19 was reduced in liver tissues of patients with chronic liver disease caused by HCV and cells infected with HCV. Also, the present inventors confirmed that GRIM19 overexpression has an effect of inhibiting HCV replication. Thereby, the present inventors completed the present invention.

DETAILED DESCRIPTION OF THE INVENTION

Technical Problem

It is an object of the present invention to provide a pharmaceutical composition for preventing or treating a hepatitis C virus infectious disease, comprising at least one selected from the group consisting of GRIM19 protein or a fragment thereof, and a gene encoding the protein or the fragment thereof.

It is another object of the present invention to provide an antiviral composition against hepatitis C virus, comprising at least one selected from the group consisting of GRIM19 protein or a fragment thereof, and a gene encoding the protein or the fragment thereof.

It is yet another object of the present invention to provide a method for treating a hepatitis C virus infectious disease, comprising administering to a subject with the hepatitis C virus infectious disease at least one selected from the group consisting of GRIM19 protein or a fragment thereof, and a gene encoding the protein or the fragment thereof.

Technical Solution

According to an aspect for achieving the above objects, the present invention relates to a pharmaceutical composition for preventing or treating a hepatitis C virus infectious disease, comprising at least one selected from the group consisting of GRIM19 protein or a protein fragment, and a gene encoding the protein or the fragment thereof.

According to another aspect, the present invention relates to an antiviral composition against hepatitis C virus, comprising at least one selected from the group consisting of GRIM19 protein or a protein fragment, and a gene encoding the protein or the fragment thereof.

According to yet another aspect, the present invention relates to a method for treating a hepatitis C virus infectious disease, comprising administering to a subject with the hepatitis C virus infectious disease at least one selected from the group consisting of GRIM19 protein or a fragment thereof, and a gene encoding the protein or the fragment thereof.

The GRIM19 protein may consist of the amino acid sequence of SEQ ID NO: 2.

Further, the gene encoding GRIM19 protein may consist of the base sequence of SEQ ID NO: 1.

The fragment of GRIM19 protein may be at least one selected from the group consisting of a protein fragment comprising the $1^{st}$ to $36^{th}$ amino acids of the amino acid sequence of SEQ ID NO: 2; a protein fragment comprising the $37^{th}$ to $72^{nd}$ amino acids of the amino acid sequence of SEQ ID NO: 2; a protein fragment comprising the $73^{rd}$ to $101^{st}$ amino acids of the amino acid sequence of SEQ ID NO: 2; and a protein fragment comprising the $102^{nd}$ to $144^{th}$ amino acids of the amino acid sequence of SEQ ID NO: 2.

For example, the fragment of GRIM19 protein may consist of an amino acid sequence selected from the group consisting of SEQ ID NO: 6, SEQ ID NO: 8, SEQ ID NO: 10, and SEQ ID NO: 12.

Further, the gene encoding the fragment of GRIM19 protein may be at least one selected from the group consisting of a gene comprising the $3^{rd}$ to $108^{th}$ bases of the base sequence of SEQ ID NO: 1; a gene comprising the $109^{th}$ to $216^{th}$ bases of the base sequence of SEQ ID NO: 1; a gene comprising the $217^{th}$ to $303^{rd}$ bases of the base sequence of SEQ ID NO: 1; and a gene comprising the $304^{th}$ to $432^{nd}$ bases of the base sequence of SEQ ID NO: 1.

For example, the gene encoding the fragment of GRIM19 protein may consist of a base sequence selected from the group consisting of SEQ ID NO: 7, SEQ ID NO: 9, SEQ ID NO: 11, and SEQ ID NO: 13.

The GRIM19 protein or a fragment thereof may further comprise a cell penetrating peptide at the N-terminus, C-terminus, or both termini.

For example, the cell penetrating peptide may consist of an amino acid sequence selected from the group consisting of SEQ ID NO: 19, SEQ ID NO: 20, SEQ ID NO: 21, and SEQ ID NO: 22.

The gene encoding GRIM19 protein or a fragment thereof may be provided in a form included in a recombinant vector.

The composition may further comprise a substance inhibiting the expression or activity of diacylglycerol acyltransferase-1 (DGAT-1).

For example, the substance inhibiting the expression or activity of DGAT-1 may be siRNA, shRNA, or antisense oligonucleotide, specifically binding to the gene or mRNA of DGAT-1.

For example, the substance inhibiting the expression or activity of DGAT-1 may be an antibody, an aptamer, or a compound of Formula 1:

[Formula 1]

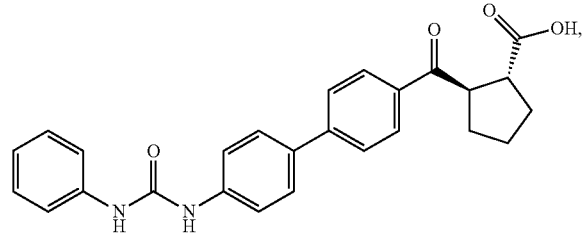

or a salt thereof, specifically binding to DGAT-1.

Further, the composition may further comprise a substance inhibiting the expression or activity of RNA-dependent RNA polymerase.

For example, the substance inhibiting the expression or activity of RNA-dependent RNA polymerase may be a compound of Formula 2:

[Formula 2]

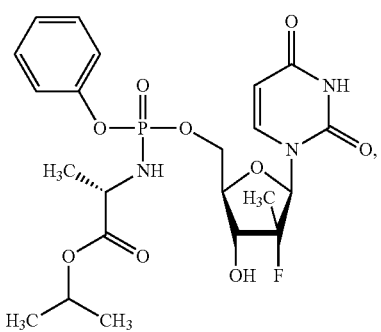

or a salt thereof.

Further, the composition may further comprise a substance activating AMP-activated protein kinase (AMPK).

For example, the substance activating AMP-activated protein kinase (AMPK) may be metformin.

The hepatitis C virus infectious disease may be hepatitis C, liver fibrosis caused by hepatitis C virus, liver cirrhosis caused by hepatitis C virus, and liver cancer caused by hepatitis C virus.

Hereinafter, the present invention is described in more detail.

The present invention has confirmed that GRIM19 overexpression has an effect of inhibiting HCV replication based on the fact that the expression of GRIM19 is reduced in liver tissues of patients with chronic liver disease caused by HCV and cells infected with HCV. The present invention provides a pharmaceutical composition for preventing or treating a hepatitis C virus infectious disease or an antiviral composition against hepatitis C virus, comprising at least one selected from the group consisting of the GRIM19 protein or a fragment thereof, and a gene encoding the protein or the fragment thereof.

Also, the present invention provides a method for treating a hepatitis C virus infectious disease, comprising administering to a subject with the hepatitis C virus infectious disease at least one selected from the group consisting of GRIM19 protein or a fragment thereof, and a gene encoding the protein or the fragment thereof.

According to an embodiment of the present invention, the expression level of GRIM19 in liver tissues of patients with chronic liver disease caused by HCV and HCV infected cells was measured using Western blot. As a result, it was confirmed that the expression of GRIM19 was specifically decreased in tissues of patients with chronic liver disease caused by HCV and cells infected with hepatitis C virus cell culture (HCVcc) (HCV obtained from cells cultured through HCV infection model established by in vitro cell culture) (see Examples 1 and 2).

According to another embodiment of the present invention, in order to evaluate the effect on HCV replication when the expression of GRIM19 was artificially increased, GRIM19 overexpression vector was prepared and transfected into HCV infected cells. As a result, it was confirmed that HCV RNA was decreased by about 60 to 70% in HCV infected cells (see Example 3).

In another example, in order to evaluate whether the inhibition of HCV replication by GRIM19 overexpression is associated with lipid accumulation in cells, the cells where GRIM19 was overexpressed were treated with lipid, and the level of HCV RNA was evaluated. As a result, it was confirmed that in the case of GRIM19 overexpression, the level of HCV RNA was decreased and the degree of lipid accumulation in Huh7 cells was decreased, whereas in the case of treatment with lipid, the level of HCV RNA was restored (see Example 4).

Further, in order to confirm the mechanism that the degree of lipid accumulation in cells is decreased when GRIM19 is overexpressed, a change in expression of acetyl-CoA carbosylase (Acc), an enzyme promoting fatty acid synthesis, was examined. As a result, it was confirmed that when GRIM19 was overexpressed, the expression of acetyl-CoA carbosylase was decreased (see Example 5).

In addition, the level of HCV RNA was evaluated when the cells where GRIM19 was overexpressed were treated with a substance inhibiting the activity of acetyl-CoA carbosylase. As a result, it was confirmed that a synergistic effect of inhibiting HCV was achieved from treatment with a substance inhibiting the activity of acetyl-CoA carbosylase (see Example 6).

In addition, the level of HCV RNA was evaluated through quantitative real-time RT PCR when the cells where GRIM19 was overexpressed were simultaneously treated with the inhibitor of DGAT-1. As a result, it was confirmed that a synergistic effect of inhibiting HCV was achieved from treatment with the inhibitor of DGAT-1 (see Example 7).

In another example of the present invention, the level of HCV RNA was evaluated when the cells where GRIM19 was overexpressed were treated with a substance inhibiting the activity of RNA-dependent RNA polymerase. As a result, it was confirmed that in the case of treatment of a substance inhibiting the activity of RNA-dependent RNA polymerase simultaneously with overexpression of GRIM19, a synergistic effect of inhibiting HCV was achieved, as compared with the case of overexpression of GRIM19 or treatment with a substance inhibiting the activity of RNA-dependent RNA polymerase, alone (see Example 8).

In another example of the present invention, GRIM19 protein was fragmented into four domains to identify domains which have an anti-HCV effect. As a result, it was confirmed that all of the cases where HCV infected Huh7 cells were transfected with each of four domains fragmented according to the present invention can significantly decrease the level of HCV RNA (see Example 9).

Further, in order to check whether an anti-HCV effect is shown when penetrating each domain itself of GRIM19 protein into cells, the effect was evaluated in HCV infection model by synthesizing cell permeable peptide sequences (CP) in each domain. As a result, it was confirmed that the level of HCV RNA can also be significantly decreased in HCV infected cells when each domain of GRIM19 protein is permeated directly into cells (see Example 10).

Therefore, the present invention proves that when the expression of GRIM19 is increased in cells by direct treatment of GRIM19 protein or a protein fragment, overexpression of GRIM19 protein or a protein fragment, or introduction of a gene encoding GRIM19 protein, the replication of hepatitis C virus is inhibited, thereby enabling to use it for preventing or treating a hepatitis C virus infectious disease.

As used herein, the term "GRIM19" is known as a protein involved in apoptosis occurring during treatment of IFN/retinoid, and is also known as NADH dehydrogenase [ubiquinone] 1 alpha subcomplex subunit 13 (NDUFA13), which is a component of mitochondrial respiratory complex 1. Further, there is no report on GRIM19 in relation with HCV. GRIM19 gene sequence of SEQ ID NO: 1 is known as Genebank Accession No. AF286697, and GRIM19 protein amino acid sequence of SEQ ID NO: 2 is known as AAG28167 (NCBI), respectively.

TABLE 1

| SEQ ID NO: 1 | atggcggcgtcaaaggtgaagcaggacatgcctccg<br>ccgggggggctatgggcccatcgactacaaacggaac<br>ttgccgcgtcgaggactgtcgggctacagcatgctg<br>gccatagggattggaaccctgatctacgggcactgg<br>agcataatgaagtggaaccgtgagcgcaggcgccta<br>caaatcgaggacttcgaggctcgcatcgcgctgttg<br>ccactgttacaggcagaaaccgaccggaggaccttg<br>cagatgcttcgggagaacctggaggaggaggccatc<br>atcatgaaggacgtgcccgactggaaggtgggggag<br>tctgtgttccacacaaccgctgggtgccccccttg<br>atcggggagctgtacgggctgcgcaccacagaggag<br>gctctccatgccagccacggcttcatgtggtacacg<br>tag |
|---|---|
| SEQ ID NO: 2 | MAASKVKQDMPPPGGYGPIDYKRNLPRRGLSGYSML<br>AIGIGTLIYGHWSIMKWNRERRRLQIEDFEARIALL<br>PLLQAETDRRTLQMLRENLEEEAIIMKDVPDWKVGE<br>SVFHTTRWVPPLIGELYGLRTTEEALHASHGFMWYT |

According to an aspect, the present invention relates to a pharmaceutical composition for preventing or treating a hepatitis C virus infectious disease, comprising at least one selected from the group consisting of GRIM19 protein or a fragment thereof, and a gene encoding the protein or the fragment thereof.

The GRIM19 protein may consist of the amino acid sequence of SEQ ID NO: 2. According to the present invention, however, GRIM19 protein may comprise a form where at least one amino acid residue is modified within the scope not generally altering the activity of molecules. Amino acid substitutions in proteins and peptides, which do not generally alter the activity of molecules, are known in the art. The most common substitutions occur between amino acid residues Ala/Ser, Val/Ile, Asp/Glu, Thr/Ser, Ala/Gly, Ala/Thr, Ser/Asn, Ala/Val, Ser/Gly, Thr/Phe, Ala/Pro, Lys/Arg, Asp/Asn, Leu/Ile, Leu/Val, Ala/Glu, and Asp/Gly. In some cases, amino acids may be modified by phosphorylation, sulfation, acetylation, glycosylation, methylation, farnesylation, etc.

Further, the present invention comprises in the scope of the present invention a protein having an amino acid sequence with at least 70%, preferably at least 75%, more preferably at least 85%, still more preferably at least 90%, or most preferably at least 95% homology with the amino acid sequence of GRIM19, as long as it retains GRIM19 protein activity.

Further, the protein fragment refers to a consecutive partial sequence among the full sequence of GRIM19 protein. For example, the protein fragment may be a protein fragment comprising consecutive 29 to 144 amino acids in GRIM19 protein; a protein fragment comprising 30 to 144 consecutive amino acids in GRIM19 protein; a protein fragment comprising 36 to 144 consecutive amino acids in GRIM19 protein; a protein fragment comprising 37 to 144 consecutive amino acids in GRIM19 protein; a protein fragment comprising 43 to 144 consecutive amino acids in GRIM19 protein, etc., but is not limited thereto.

As another example, the protein fragment may be a protein fragment comprising the $1^{st}$ to $36^{th}$ amino acids of the amino acid sequence of SEQ ID NO: 2; a protein fragment comprising the $37^{th}$ to $72^{nd}$ amino acids of the amino acid sequence of SEQ ID NO: 2; a protein fragment comprising the $73^{rd}$ to 100 amino acids of the amino acid sequence of SEQ ID NO: 2; a protein fragment comprising the $102^{nd}$ to $144^{th}$ amino acids of the amino acid sequence of SEQ ID NO: 2, etc., but is not limited thereto.

As another example, the protein fragment may be SEQ ID NO: 6, 8, 10, or 12, but may comprise a form where at least one amino acid residue is modified within the scope of not generally altering the activity of GRIM19 protein fragment. Further, the present invention comprises in the scope of the present invention a protein having an amino acid sequence with at least 70%, preferably at least 75%, more preferably at least 85%, still more preferably at least 90%, or most preferably at least 95% homology with the amino acid sequence of GRIM19, as long as it retains GRIM19 protein activity.

The gene encoding the protein is comprised in the scope of the present invention as long as it corresponds to a gene encoding GRIM19 protein, and may consist of, for example, the base sequence of SEQ ID NO:1, but is not limited thereto.

Further, the present invention comprises in the scope of the present invention a gene having a DNA sequence with at least 70%, preferably at least 75%, more preferably at least 85%, still more preferably at least 90%, or most preferably at least 95% homology with the gene sequence encoding GRIM19 protein, as long as it retains GRIM19 protein activity.

The gene encoding the protein is comprised in the scope of the present invention as long as it corresponds to a gene encoding the fragment of GRIM19 protein. For example, the gene may be a gene comprising the $3^{rd}$ to $108^{th}$ bases of the base sequence of SEQ ID NO: 1; a gene comprising the $109^{th}$ to $216^{th}$ bases of the base sequence of SEQ ID NO: 1; a gene comprising the $217^{th}$ to $303^{rd}$ bases of the base sequence of SEQ ID NO: 1; a gene comprising the $304^{th}$ to $432^{nd}$ bases of the base sequence of SEQ ID NO: 1, etc., but is not limited thereto.

As another example, the gene encoding the protein fragment may consist of a base sequence of SEQ ID NO: 7, 9, 11, or 13, but is not limited thereto.

Further, the present invention comprises in the scope of the present invention a gene having a DNA sequence with at least 70%, preferably at least 75%, more preferably at least 85%, still more preferably at least 90%, or most preferably at least 95% homology with the gene sequence encoding GRIM19 protein, as long as it retains GRIM19 protein activity.

According to an example of the present invention, the protein or a fragment thereof may further comprise a cell penetrating peptide at the N-terminus, C-terminus, or both termini. The protein or a fragment thereof can exhibit excellent anti-HCV activity by comprising the cell penetrating peptide, thereby effectively penetrating HCV infected cells.

The cell penetrating peptide may be, for example, R9 peptide (RRRRRRRRR, SEQ ID NO: 19), Penetratin peptide (RQIKIWFQNRRMKWKK, SEQ ID NO: 20), TAT peptide (GRKKRRQRRRPPQ, SEQ ID NO: 21), MTS peptide (AAVALLPAVLLALLAP, SEQ ID NO: 22), but peptides having the activity that can penetrate cells belong to the scope of the present invention with no limitation.

The method for obtaining the GRIM19 protein or protein fragment is not specifically limited. For example, the protein or protein fragment may be extracted from natural sources or synthesized (Merrifield, J. Amer. chem. Soc. 85:2149-2154, 1963), or may be prepared using a gene recombination method based on DNA sequences.

The gene encoding GRIM19 protein or a protein fragment of the present invention refers to nucleic acid molecules encoding information of amino acids of GRIM19 protein or protein fragment and may be isolated from nature or artificially synthesized and transformed. In other words, the gene is not limited to wild-type DNA and refers to a gene that can be suitably used for the objects of the present invention, regardless of whether proper modification is applied or an element for regulating expression is added within the scope of retaining the activity which expresses GRIM19 protein or a protein fragment, or the gene is obtained by a genetic engineering or chemical process.

Further, the gene encoding GRIM19 protein or a fragment thereof of the present invention may be provided by being included in a recombinant vector for intracellular transmission. In this case, the gene encoding GRIM19 protein or a protein fragment may bind to expression regulatory sequences comprising promotor/enhancer sequences and other sequences necessary for transcription, translation or processing, in an expression vector. Regulatory sequences may not only indicate constitutive expression of nucleotide, but include tissue-specific regulatory and/or inductive sequences. The design of expression vector may be determined by factors such as host cells to be transformed, targeted expression level, etc.

In the composition of the present invention, as vectors into which the gene encoding GRIM19 protein or a protein fragment can be inserted, virus-derived vectors including retrovirus vectors, adenovirus vectors, adeno-associated virus vectors, or herpes simplex virus vectors, and plasmids that can be expressed in the body of animals and their modified vectors may be used.

According to an example of the present invention, the composition according to the present invention may further comprise a substance inhibiting the expression or activity of DGAT-1, thereby having a synergistic effect of inhibiting hepatitis C virus replication, as compared with the case of treatment of the composition according to the present invention alone. DGAT-1 is known as an enzyme producing triglycerides from diacylglycerol and acyl-CoA. DGAT gene sequence of SEQ ID NO: 17 is known as Genebank Accession No. NM_012079.5, GI:525342626 (NCBI), and DGAT protein amino acid sequence of SEQ ID NO: 18 is known as NP_036211.2 (NCBI), respectively.

The substance inhibiting the expression or activity of DGAT-1 refers to a substance blocking synthesis pathway, reaction pathway, etc. of DGAT-1. For example, the substance may be siRNA, shRNA, or antisense oligonucleotide, etc., that can complementarily bind (hybridization) to mRNA of DGAT-1 gene. Preferably, the siRNA, shRNA, or antisense oligonucleotide specifically binds to the base sequence of mRNA of DGAT-1 gene and does not specifically bind to the base sequence of other nucleic acid substances. However, the substance is not limited thereto if it corresponds to a substance blocking synthesis pathway, reaction pathway, etc. of DGAT-1.

Here, complementary binding means that antisense oligonucleotide is sufficiently complementary to selectively hybridize to mRNA target of DGAT-1 gene under predetermined hybridizing or annealing conditions, preferably under physiological conditions, with both meanings of substantially complementary and perfectly complementary, preferably perfectly complementary.

As an example, siRNA may be sufficiently complementary to selectively hybridize to mRNA target of DGAT-1 gene of the present invention. The term "siRNA" refers to a double-stranded RNA that can induce RNA interference (RNAi) through cleavage of specific mRNA. The siRNA consists of a sense RNA strand having a sequence identical to mRNA of a target gene and an antisense RNA strand having a complementary sequence thereto. As the siRNA can inhibit the expression of a target gene, it may be provided as an efficient method for knockdown of genes or a method for treatment of genes.

The siRNA is not limited to those in which double-stranded RNA portions constitute complete pairs, but may include unpaired portions such as mismatch (corresponding bases are not complementary), bulge (lacking corresponding base in one strand), etc. The total length of the siRNA may be 10 to 100 bases, preferably 15 to 80 bases, and more preferably 20 to 70 bases. The terminal structure of siRNA may be blunt or cohesive as long as it can inhibit the expression of a target gene by RNAi effect. The cohesive terminal structure may be 3'-terminal overhang or 5'-terminal overhang. The number of overhanging bases is not limited. Further, the siRNA may include, for example, at the overhang on one terminal lower molecular weight RNA (for example, natural RNA molecules such as tRNA, rRNA, and viral RNA, or artificial RNA molecules) within the scope that can retain the effect of inhibiting the expression of a target gene. The terminal structure of siRNA is not necessarily to have the cut off structure at both ends, and may have a stem-loop structure in which terminals of one side of double-stranded RNA are connected by a linker RNA.

The siRNA used in the present invention may be in a complete form of polynucleotide pairing as it is, i.e., a form in which siRNA is directly synthesized in vitro and introduced into cells through transfection, or a form in which siRNA can be induced from a single-stranded polynucleotide where one single-stranded oligonucleotide fragment and its reverse complement are separated by a spacer so as to have such form after in vivo administration, for example, a form that siRNA expression vector prepared such that siRNA is expressed in cells or PCR-induced siRNA expression cassette is introduced into cells through transfection or infection. The determination of a method for preparing siRNA and introducing it into cells or animals may vary depending on the purpose and cellular biological functions of a target gene product.

As another example, shRNA may be sufficiently complementary to selectively hybridize to mRNA target of DGAT-1 gene of the present invention. The term "shRNA" is to overcome the disadvantages of siRNA, including high biosynthesis costs, low cell transfection efficiency which results in short-term persistence of RNA interference effect, etc. The shRNA can be expressed from a promoter of RNA polymerase III using an adenoviral, lentiviral and plasmid expression vector system, having it introduced into cells. The shRNA is well known to turn into siRNA having an accurate structure by a siRNA processing enzyme (Dicer or RNase III) present in cells and induce silencing of a target gene.

As another example, antisense oligonucleotide may be sufficiently complementary to selectively hybridize to mRNA target of DGAT-1 gene of the present invention. The term "antisense oligonucleotide" refers to DNA, RNA or a derivative thereof containing a complementary sequence to a specific mRNA sequence, thus binding to the complementary sequence in mRNA and inhibiting translation of mRNA into a protein. The antisense sequence of the present invention refers to a sequence of DNA or RNA that is complementary to mRNA of DGAT-1 gene and can bind to mRNA of DGAT-1 gene, and may inhibit the translation of mRNA of DGAT-1 gene, translocation into cytoplasm, maturation, or any other activity essential to overall biological functions. The length of the antisense oligonucleotide may be 6 to 100 bases, preferably 8 to 60 bases, and more preferably 10 to 40 bases.

The antisense RNA may be synthesized in vitro by a typical method and administered in vivo, or may be synthesized in vivo. An example of synthesizing antisense RNA in vitro is to use RNA polymerase I. An example of synthesizing antisense RNA in vivo is to use a vector containing the origin of a multicloning site (MCS) in opposite direction, so that antisense RNA is transcribed. Such antisense RNA preferably contains a translation stop codon in its sequence to prevent translation into a peptide sequence.

In addition to further inclusion of at least one of siRNA or shRNA of DGAT-1 or DGAT-1 antisense oligonucleotide, the composition of the present invention may comprise a further substance for preventing or treating a hepatitis C virus infectious disease in patients, or may use a formulation promoting introduction of siRNA or antisense oligonucleotide molecules, for example, liposome (U.S. Pat. Nos. 4,897,355; 4,394,448; 4,235,871; 4,231,877; 4,224,179; 4,753,788; 4,673,567; 4,247,411; 4,814,270) or combine with at least one lipophilic carrier of various types of sterols including cholesterol, cholate, and deoxycholic acid. Further, the antisense oligonucleotide may be conjugated to a peptide absorbed by cells. Examples of useful peptides may comprise peptide hormones, antigens or antibodies, peptide toxins, etc.

Other examples of the substance inhibiting the expression or activity of DGAT-1 may comprise an antibody against DGAT-1; an aptamer; or a compound of Formula 1 (A922500, MERK):

[Formula 1]

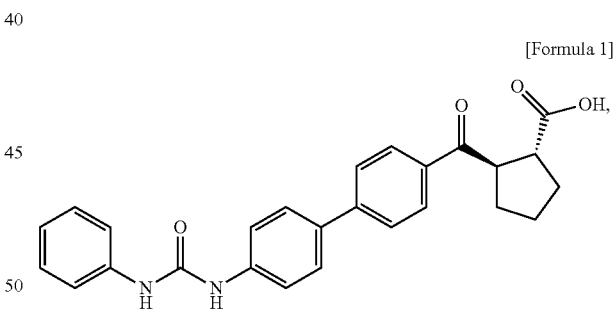

or a salt thereof.

The term "antibody", known in the pertinent art, refers to a specific protein molecule that indicates an antigenic region. With respect to the objects of the present invention, the antibody specifically binds to DGAT-1 protein of the present invention. To prepare this antibody, DGAT-1 gene is cloned into an expression vector according to a typical method, to obtain DGAT-1 protein encoded by the DGAT-1 gene, and then the antibody may be prepared from the obtained DGAT-1 protein according to a typical method. Here, partial peptides that can be produced from the DGAT-1 protein are included. The partial peptide of the present invention comprises at least 7 amino acids, preferably 9 amino acids, and more preferably 12 or more amino acids. The form of the antibodies of the present invention is not specifically limited, and the antibodies of the present invention comprise polyclonal antibodies, monoclonal antibodies or fragments thereof if they have antigen binding property, and all immunoglobulin antibodies. Further, the antibodies of the present invention comprise special antibodies such as humanized antibodies.

The antibodies of the present invention which inhibit the expression or activity of DGAT-1 comprise not only complete forms having two full-length light chains and two full-length heavy chains but functional fragments of antibody molecules. The functional fragments of antibody molecules refer to fragments retaining at least an antigen-binding function, and include Fab, F(ab'), F(ab')$_2$, Fv, etc.

The term "aptamer" refers to a nucleic acid molecule with binding activity to a specific target molecule. The aptamer can inhibit activity of a specific target molecule by binding to the specific target molecule. The aptamer of the present invention may be nucleic acids in linear or annular shape, such as RNA, DNA, modified nucleic acid, or a mixture thereof. The aptamer, like a peptide generated by phage display or monoclonal antibodies (MAbs), can specifically bind to a selected target and regulate activity of the target. For example, the aptamer can block the target's ability to function through binding. Created by an in vitro selection process from pools of random sequence oligonucleotides, the aptamer was generated for at least 100 proteins including growth factors, transcription factors, enzymes, immunoglobulins, and receptors. A typical aptamer is 10-15 kDa in size (30-45 nucleotides), binds its target with sub-nanomolar affinity, and discriminates against closely related targets (for example, the aptamer does not typically bind to other proteins from the same gene family). The aptamer can specifically bind to a selected target, regulate activity of the target, and block the target's ability through the same types of binding interactions (for example, hydrogen bonding, electrostatic complementarity, hydrophobic contacts, and steric exclusion) that drive affinity the aptamer has and specificity in antibody-antigen complexes.

The "aptamer" of the present invention has binding activity to DGAT-1. Preferably, the aptamer of the present invention can inhibit formation of HCV particles by binding to DGAT-1.

According to another example of the present invention, the composition according to the present invention may further comprise a substance inhibiting the expression or activity of RNA-dependent RNA polymerase, thereby having a synergistic effect of inhibiting hepatitis C virus replication, as compared with the case of treatment of the composition according to the present invention alone.

The substance inhibiting the expression or activity of RNA-dependent RNA polymerase refers to a substance blocking synthesis pathway, reaction pathway, etc. of RNA-dependent RNA polymerase. For example, the substance may be a compound of Formula 2:

[Formula 2]

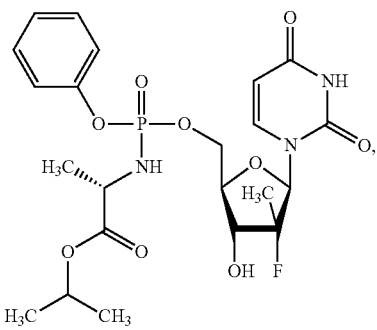

or a salt thereof.

Further, the explanation above on the substance inhibiting the expression or activity of DGAT-1 may apply to the explanation on the terms related to the substance inhibiting the expression or activity of RNA-dependent RNA polymerase.

According to yet another example of the present invention, the composition according to the present invention may further comprise a substance activating AMP-activated protein kinase (AMPK), thereby having a synergistic effect of inhibiting hepatitis C virus replication, as compared with the case of treatment of the composition according to the present invention alone.

The substance activating AMP-activated protein kinase refers to a substance activating or promoting synthesis pathway, reaction pathway, etc. of AMP-activated protein kinase. For example, the substance may be metformin.

According to the present invention, the hepatitis C virus infectious disease refers to a disease that may occur by infection with hepatitis C virus. Specifically, the hepatitis C virus infectious disease may be hepatitis C caused by hepatitis C virus, and liver fibrosis, liver cirrhosis, and liver cancer caused by hepatitis C virus, which are developed by chronic hepatitis C, but is not limited thereto. The disease may cover all diseases occurring by infection with hepatitis C virus.

According to yet another aspect, the present invention relates to an antiviral composition against hepatitis C virus, comprising at least one selected from the group consisting of GRIM19 protein or a fragment thereof, and a gene encoding the protein or the fragment thereof.

The explanation above on the pharmaceutical composition for preventing or treating a hepatitis C virus infectious disease may apply to the explanation on the terms related to the antiviral composition.

According to an embodiment, the composition of the present invention may be used alone, or may be used in combination with other therapies that are used for preventing or treating a hepatitis C virus infectious disease in order to increase treatment efficiency.

The composition according to the present invention may be administered with a pharmaceutically acceptable carrier. For oral administration, binders, lubricants, disintegrants, excipients, emulsifiers, dispersions, stabilizers, suspending agents, pigments, perfumes, etc. may be used. For injection administration, buffers, preservatives, analgesics, emulsifiers, isotonic agents, stabilizers, etc. may be mixed for use. For local administration, bases, excipients, lubricants, preservatives, etc. may be used. The composition of the present invention may be formulated with a pharmaceutically acceptable carrier as described above in various manners. For example, for oral administration, the composition of the present invention may be formulated in the form of tablet, troche, capsule, elixir, suspension, syrup, wafer, etc., and for injection administration, the composition can be formulated as a unit dosage ampoule or a multiple dosage form.

As used herein, the term "administration" means introducing the composition of the present invention into a patient using any proper manner. The composition of the present invention may be administered through any general route, as long as it can reach a desired tissue. The composition of the present invention can be administered orally, intraperitoneally, intravenously, intramuscularly, subcutaneously, transdermally, intranasally, intrapulmonarily, intrarectally, intracavitarily, intraperitoneally, or intradurally, but is not limited thereto.

The effective dose of the composition of the present invention may vary depending on various factors that are well known in the medical field, including gender, body surface area, disease type and severity, age, sensitivity to drugs, administration route and excretion rate, treatment period, target cell, expression level, etc., and may be easily determined by those skilled in the art.

Effect of Invention

The present invention provides a pharmaceutical composition for preventing or treating a hepatitis C virus infectious disease or an antiviral composition against hepatitis C virus, comprising GRIM19 protein or a protein fragment, and a gene encoding the protein or the fragment thereof. The use of the composition of the present invention can treat patients on whom the standard-of-care treatment for hepatitis C virus does not work, and treat or prevent hepatitis C virus infectious diseases by inhibiting hepatitis C virus replication, irrespective of genotype.

BEST MODE FOR CARRYING OUT INVENTION

Hereinafter, the present invention is described in detail with reference to examples. The following examples, however, are only to illustrate the present invention and the present invention is not limited to the following examples.

EXAMPLE 1

Confirmation of Decrease in GRIM19 Expression in Liver Tissue of Patients with Chronic Liver Disease Caused by HCV In order to evaluate the expression level of GRIM19 in tissue of patients with chronic liver disease (CLD) caused by infection with HBV and HCV, which are main viruses causing chronic hepatitis, Western blot analysis was performed using anti-GRIM19 antibody.

Patients with chronic hepatitis (CHB, CHC), liver cirrhosis (LC), and liver cancer (HCC) caused by infection with HBV or HCV were selected from patients approved by Institutional Review Board (IRB) among patients of Korea Seoul St. Mary's Hospital, and liver tissues subjected to biopsy was obtained therefrom. After lysing 20 mg of the obtained liver tissues (CHC n=4, LC n=3, HCC n=2, for hepatitis C patients; CHB n=3, LC n=3, HCC n=3 for hepatitis B patients) using PROPREP reagent (INTRON BIOTECHNOLOGY), Western blot analysis was performed using 20 μg of lysates. As anti-GRIM19 monoclonal antibody, a product from Abcam was used, and as anti-β-actin monoclonal antibody, a product from Sigma was used.

Figure 1:
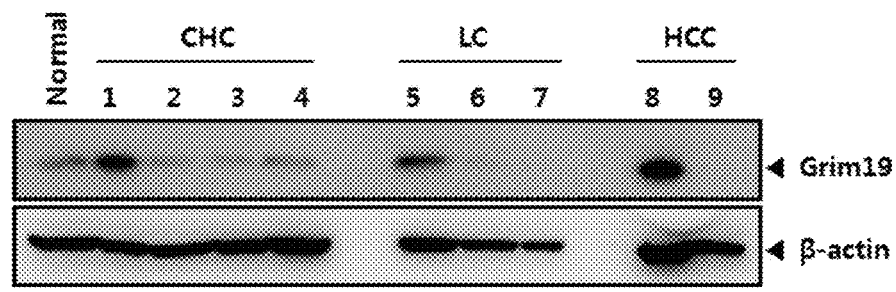
FIG. 1 shows a result of Western blot analysis of GRIM19 expression in liver tissues of patients with chronic liver disease caused by HCV. "HCV-infected patients" indicates patients infected with hepatitis C virus, "HBV-infected patients" indicates patients infected with hepatitis B virus, "CHC" indicates liver tissues of patients with chronic hepatitis C infection, "CHB" indicates liver tissues of patients with chronic hepatitis B infection. "LC" indicates liver tissues of patients with liver cirrhosis (LC), "HCC" indicates liver tissues of patients with liver cancer (HCC), "Grim19" indicates the expression of GRIM19 protein, and "β-actin" indicates the expression of β-actin protein.
Figure 1:
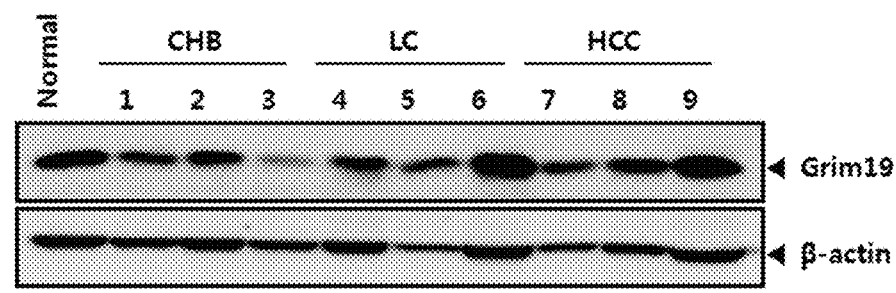
Figure 2:
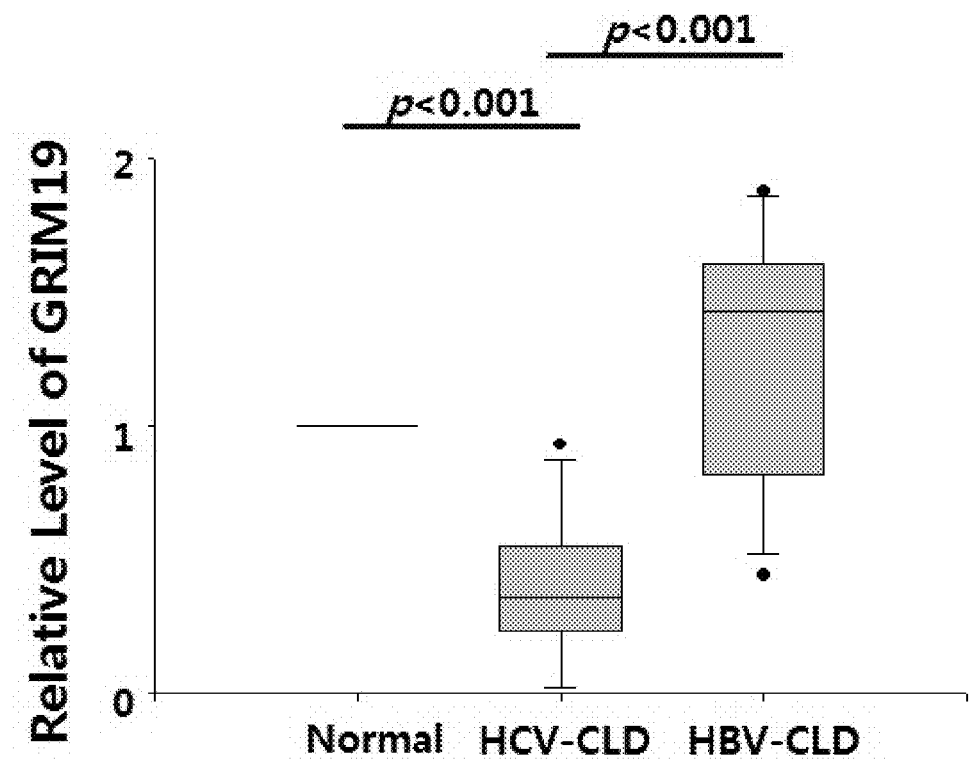
FIG. 2 is a graph showing relative comparison of GRIM19 expression in liver tissues of patients with chronic liver disease caused by HCV. "Normal" indicates normal comparative group, "HCV-CLD" indicates patients with chronic hepatitis C infected with hepatitis C virus, and "HBV-CLD" indicates patients with chronic hepatitis B infected with hepatitis B virus.

As a result of experiment, it was confirmed that unlike liver tissues of HBV infected patients, in tissues of patients with chronic liver disease caused by HCV, the expression of GRIM19 was specifically decreased (FIG. 1 and FIG. 2).

EXAMPLE 2

Confirmation of Decrease in GRIM19 Expression in In Vitro HCV Infection Model

HCV does not infect small animals such as mice, and the sole animal model is chimpanzee. Thus, most of recent studies on HCV are conducted through in vitro infection model.

Figure 13:
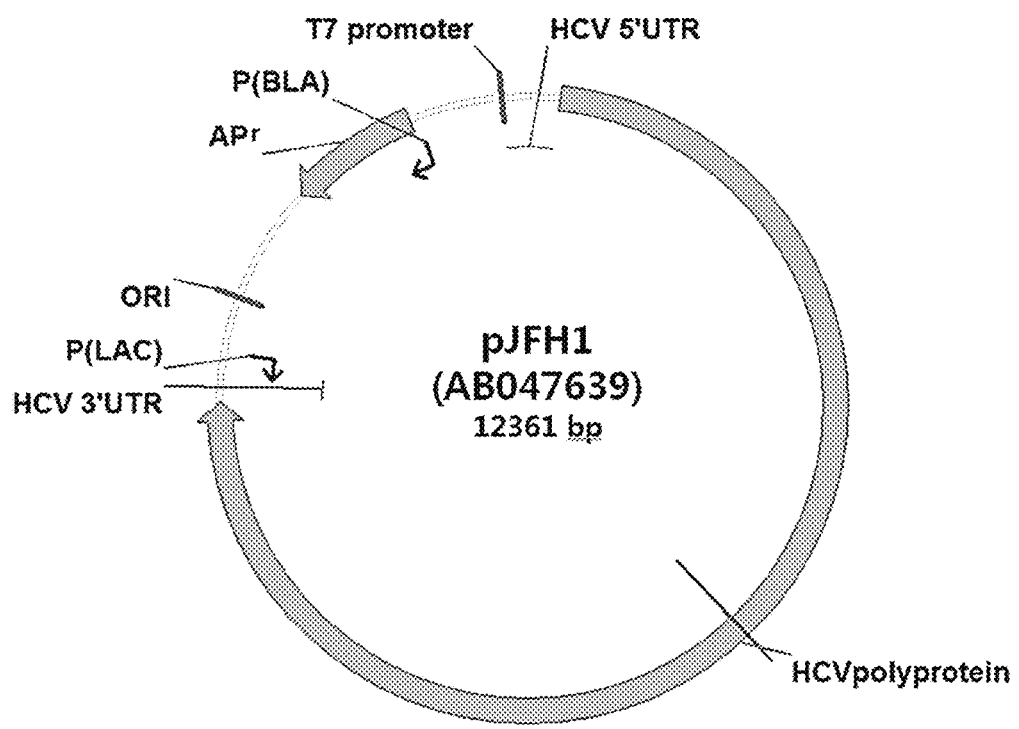
FIG. 13 shows a cleavage map that shows the structure of pJFH-1.

Hepatitis C Virus cell culture (HCV cc) system was constructed with pJFH-1 (FIG. 13), a vector comprising infectious clone JFH-1 clone provided by the research team led by professor Takaji Wakita of Japan National Institute of Infectious Diseases which constructed HCVcc using JFH-1 strain.

In order to construct a recombinant infectious HCV model, infectious HCV genome which was synthesized through in vitro transcription was introduced into Huh7 cells (Korean Cell Line Bank) through electroporation, followed by passage every three days, to culture cells.

HCV RNA in Huh7 cells after electroporation was evaluated through quantitative realtime RT PCR. The total RNA was extracted using Trizol LS reagents (Invitrogen), and cDNA was synthesized using 2 μg of the extracted RNA. Quantitative realtime RT PCR was carried out using the synthesized cDNA, Lightcycler 480 probe master (Roche), HCV 5'-UTR specific fluorescent probes (SEQ ID NO: 3), and primers (SEQ ID Nos: 4 and 5).

TABLE 2

| | Gene | Sequence (5'→3') |
|---|---|---|
| SEQ ID NO: 3 | HCV 5'UTR probe | CTGCGGAACCGGTGAGTACAC |
| SEQ ID NO: 4 | HCV 5'UTR Forward Primer | GCGCCTAGCCATGGCGTTAGT ATGAGTGTC |
| SEQ ID NO: 5 | HCV 5'UTR Reverse Primer | ACCACAAGGCCTTTCGCAACC CAACGCTAC |

Three days after electroporation, about $1\times10^6$ copies were detected per 1 μg of the total RNA. As a result of examination of the amount of HCVcc discharged into the cell culture medium through the level of HCV RNA, it was confirmed that the level of HCV RNA was retained at about $1\times10^7$ per 1 μg of RNA in 1 ml of the culture medium. From this, it was confirmed that in vitro HCV infectious system which is the experimental basis of HCV research was constructed.

A change in GRIM19 expression derived from HCV infection was examined using in vitro HCV infection system. After seeding $1.5\times10^6$ Huh7 cells in 10-cm culture dish, the cells were infected with HCVcc next day. Thereafter, every three days, cells and cell media were subcultured at a ratio of 1:4.

HCVcc infected Huh7 cells were harvested on $3^{rd}$, $6^{th}$, $9^{th}$, and $12^{th}$ days, and the expression level of GRIM19 was confirmed through Western blot analysis. After lysing cells using PROPREP reagent (INTRON BIOTECHNOLOGY), Western blot analysis was performed using 20 μg of lysates. As anti-GRIM19 monoclonal antibody, a product from Abcam was used, and as anti-β-actin monoclonal antibody, a product from Sigma was used.

Figure 3:
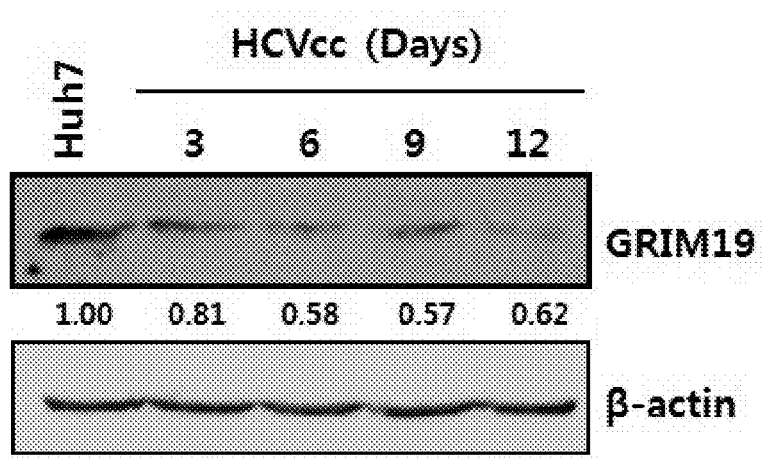
FIG. 3 shows a result of Western blot analysis of GRIM19 expression in in vitro HCV infection model. "Huh7" indicates a result before infection with HCV, and "HCVcc (Days)" indicates the number of days of infection with HCV.

As in HCV-CLD tissues (chronic hepatitis C patients infected with hepatitis C virus), it was confirmed that in HCVcc infected Huh7, the level of GRIM19 was decreased. The level was decreased by about 80% three days after infection, and by about 60% six days after infection (FIG. 3).

EXAMPLE 3

Decrease in HCV RNA Level by GRIM19 Overexpression

From Examples 1 and 2, it was confirmed that artificial increase in the expression of GRIM19 produces the effect of inhibiting HCV replication based on the deduction that the GRIM19 expression in HCV infected tissues and cells was regulated by virus in order to form environment favorable to HCV replication.

Figure 4:
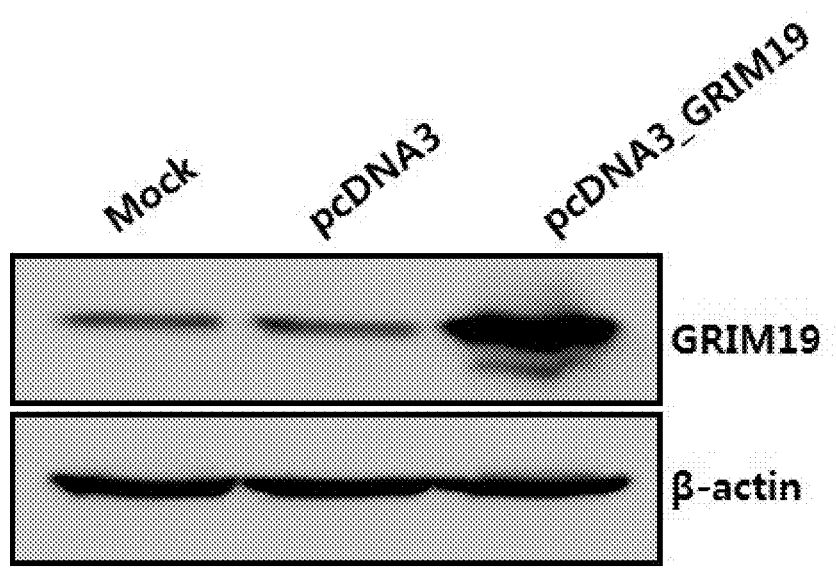
FIG. 4 shows a result of Western blot confirming GRIM19 overexpression after transfection of a vector expressing GRIM19. "Mock" indicates cells with no treatment, "pcDNA3" indicates cells transfected with a vector expressing no GRIM19, and "pcDNA3_GRIM19" indicates the result of protein expression in cells transfected with a vector expressing GRIM19.
Figure 14:
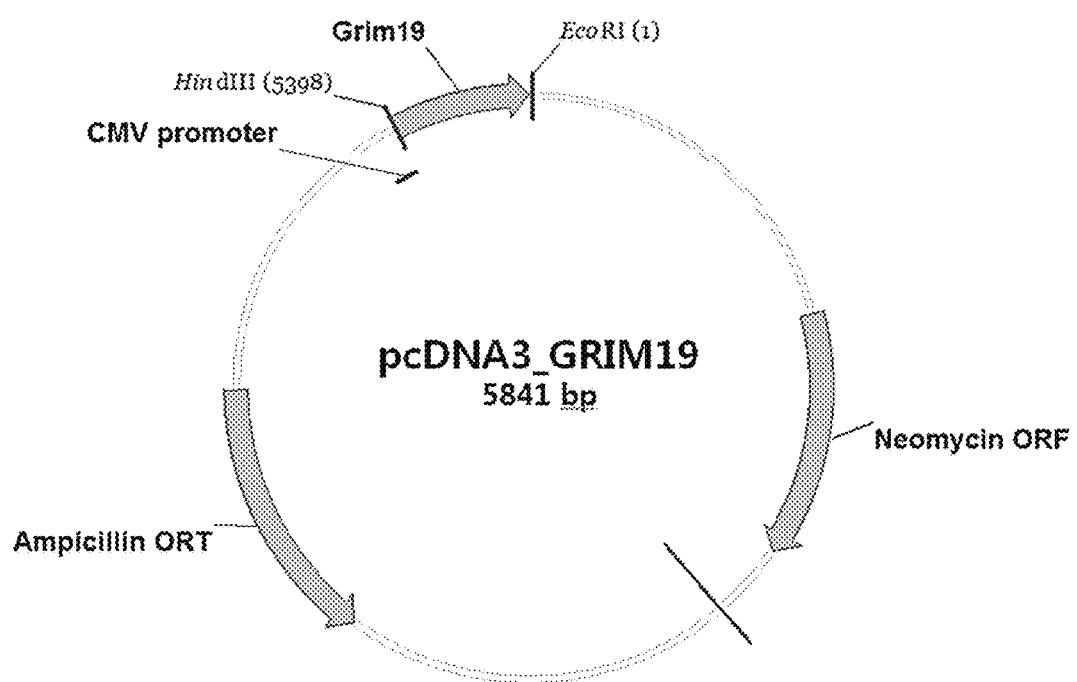
FIG. 14 shows a structure of GRIM19 overexpression vector prepared by using pcDNA3.
Figure 15:
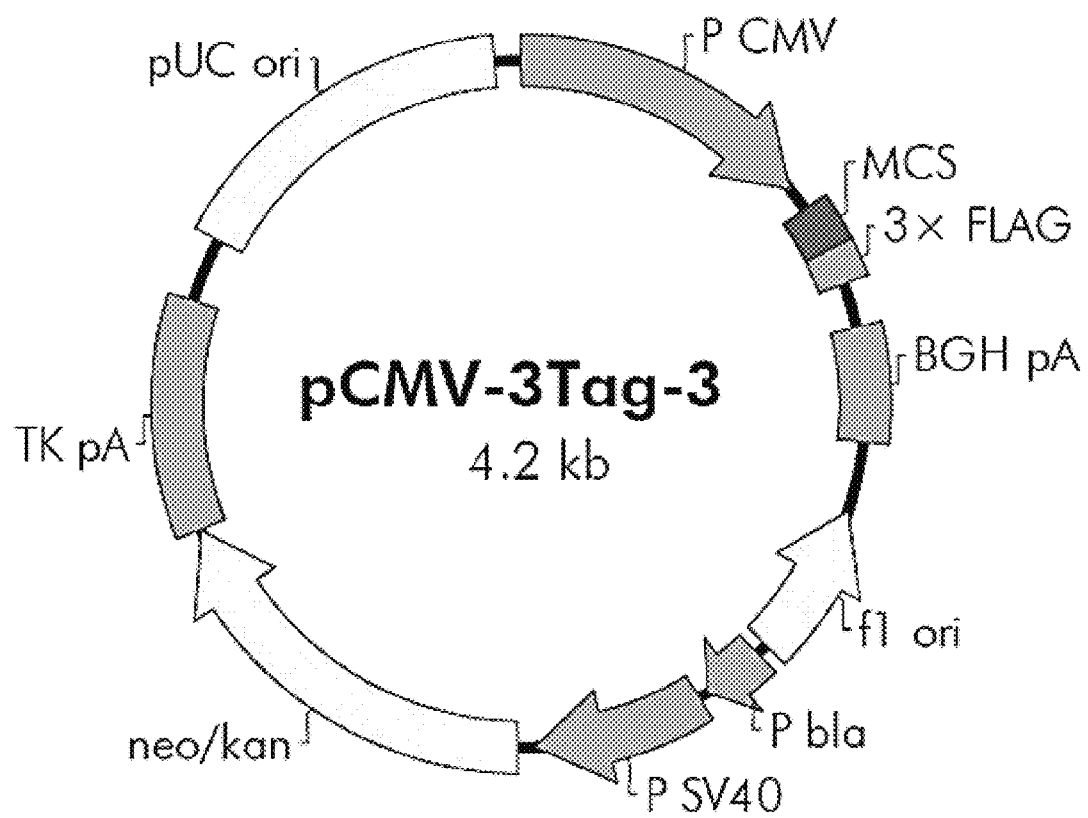
FIG. 15 shows a cleavage map that shows the structure of pCMV-3Tag-3A vector.

GRIM19 overexpression vector was prepared to evaluate the effect of inhibiting HCV replication through GRIM19 overexpression. The gene of GRIM19 was obtained from mRNA of Huh7 cells through RT PCR and cloned to pcDNA3 vector (Invitrogen) (FIG. 14) using restriction enzymes BglII and HindIII. The overexpression of GRIM19 was evaluated through Western blot analysis (FIG. 4).

After seeding $1.5\times10^6$ Huh7 cells in 10-cm culture dish, the cells were infected with HCVcc next day. Thereafter, every three days, cells and cell media were subcultured at a ratio of 1:4. The cells which were subcultured on $1^{st}$, $4^{th}$, $7^{th}$ and $10^{th}$ days of infection were transfected with 5 μg of pcDNA3_GRIM1 9 using FUGENE HD (Promega). The cells were harvested 48 hours after transfection, and the level of HCV RNA was evaluated through quantitative realtime RT PCR.

Figure 5A:
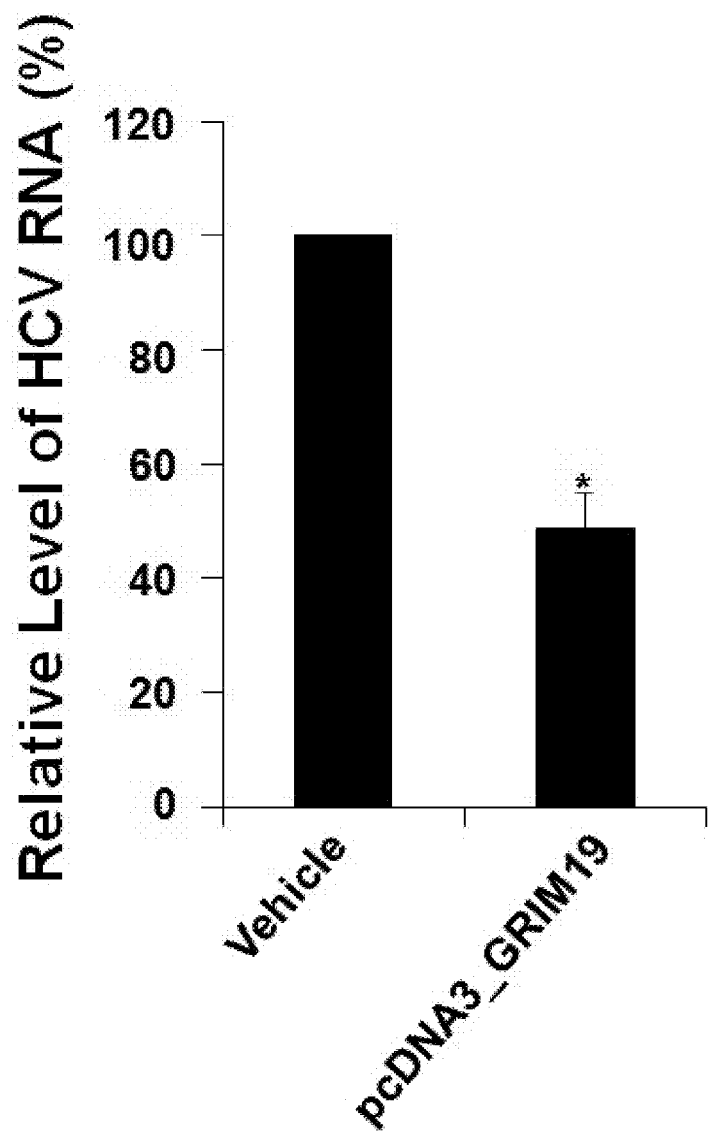
FIG. 5a shows a result confirming a change in level of HCV RNA 48 hours after transfection of Huh7 cells, which were infected with HCVcc, with pcDNA3_GRIM19.

FIG. 5a, which shows the level of HCV RNA 48 hours after transfection of Huh7 cells, which were infected with HCVcc, with pcDNA3_GRIM19, confirmed that HCV RNA was decreased when GRIM19 protein is expressed even though Huh7 cells were infected with HCVcc.

Figure 5B:
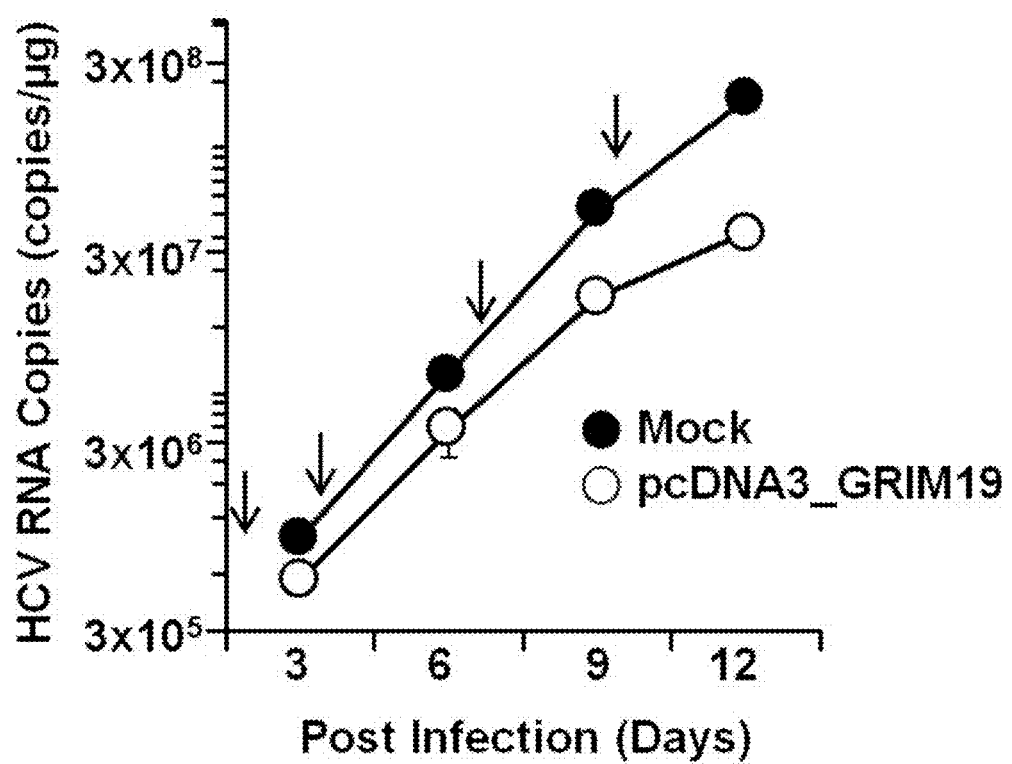
FIG. 5b shows a change in level of HCV RNA according to GRIM19 overexpression. "Mock" indicates cells with no treatment, and "pcDNA3_GRIM19" indicates the result in cells transfected with a vector expressing GRIM19.

Also, with reference to FIG. 5b, in the case of HCVcc infected Huh7 cells, about $9.5\times10^5$ HCV RNA copies per 1 μg of the total RNA on $3^{rd}$ day, about $6.9.5\times10^6$ HCV RNA copies per 1 μg of the total RNA on $6^{th}$ day, about $5.0\times10^7$ HCV RNA copies per 1 μg of the total RNA on $9^{th}$ day, and about $1.9\times10^8$ HCV RNA copies per 1 μg of the total RNA on $12^{th}$ day were detected. As a result of GRIM19 overexpression due to transfection with pcDNA3_GRIM19, the level of HCV RNA was decreased down to about $5.7\times10^5$ HCV RNA copies, $3.5\times10^6$ HCV RNA copies, $1.8\times10^7$ HCV RNA copies, and $3.8\times10^7$ HCV RNA copies, respectively. From this, it was confirmed that as a result of GRIM19 overexpression in HCV infected Huh7 cells, the level of HCV RNA was decreased by about 40 to 80%.

Therefore, it was clearly proved that the expression of GRIM19 protein in HCV infected cells has anti-HCV activity.

EXAMPLE 4

Confirmation of Association Between HCV RNA Level and Lipid Accumulation in Cells The level of HCV RNA was evaluated after treating oleic acid (OA) to Huh7 cells transfected with pcDNA3_GRIM19, in order to confirm whether the effect of decrease in HCV RNA by GRIM19 overexpression is associated with lipid accumulation in cells, based on the fact that HCV replication is known to be much affected by lipid in cells.

The degree of lipid accumulated in cells was evaluated by measuring the degree of fluorescence after Nile Red staining. Specifically, after seeding $2 \times 10^5$ Huh7 cells in 6 well plates, the cells were transfected with pcDNA3_GRIM19 after 24 hours. After transfection with pcDNA3_GRIM19, the cells were cultured using serum free DMEM media. After 24 hours, the cells transfected with pcDNA3_GRIM19 were treated with 100 μM of oleic acid (OA) using serum free DMEM media supplemented with 1% BSA. After 24 hours, the amount of lipid in cells, increased by OA treatment, was evaluated through Nile Red staining. The cells in which pcDNA3_GRIM19 was overexpressed and OA treatment was completed were fixed using 3.7% paraformaldehyde, and the lipid in cells was subjected to fluorescence staining using PBS solution including 1 μg/ml of Nile Red. The nucleus was stained using 0.2 μg/ml of DAPI in order to predict the degree of lipid accumulation for the number of cells. The degree of lipid accumulation in cells was evaluated through the intensity of fluorescence measured by a microplate reader, and the degree of lipid accumulation was relatively compared and analyzed through the degree of DAPI.

Figure 6A:
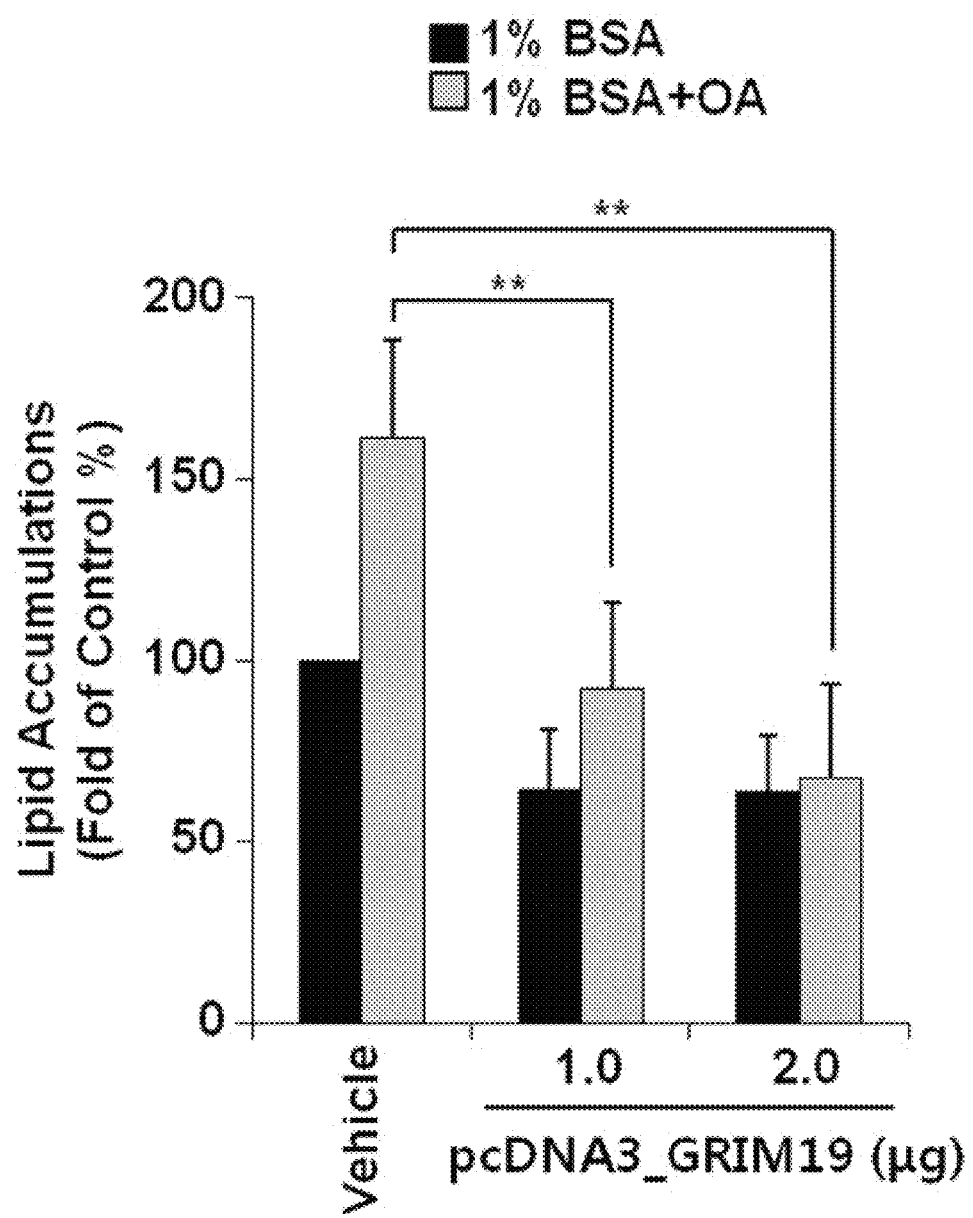
FIG. 6a shows a change in degree of lipid accumulation in Huh7 cells when a vector expressing GRIM19 was transfected and GRIM19 was overexpressed. "BSA" indicates the case of addition of bovine serum albumin as control group, and "OA" indicates the case of addition of oleic acid.

As a result, with reference to FIG. 6a, it was confirmed that in the case of GRIM19 overexpression due to transfection with pcDNA3_GRIM19, the degree of lipid accumulated in Huh7 cells was decreased.

Figure 6B:
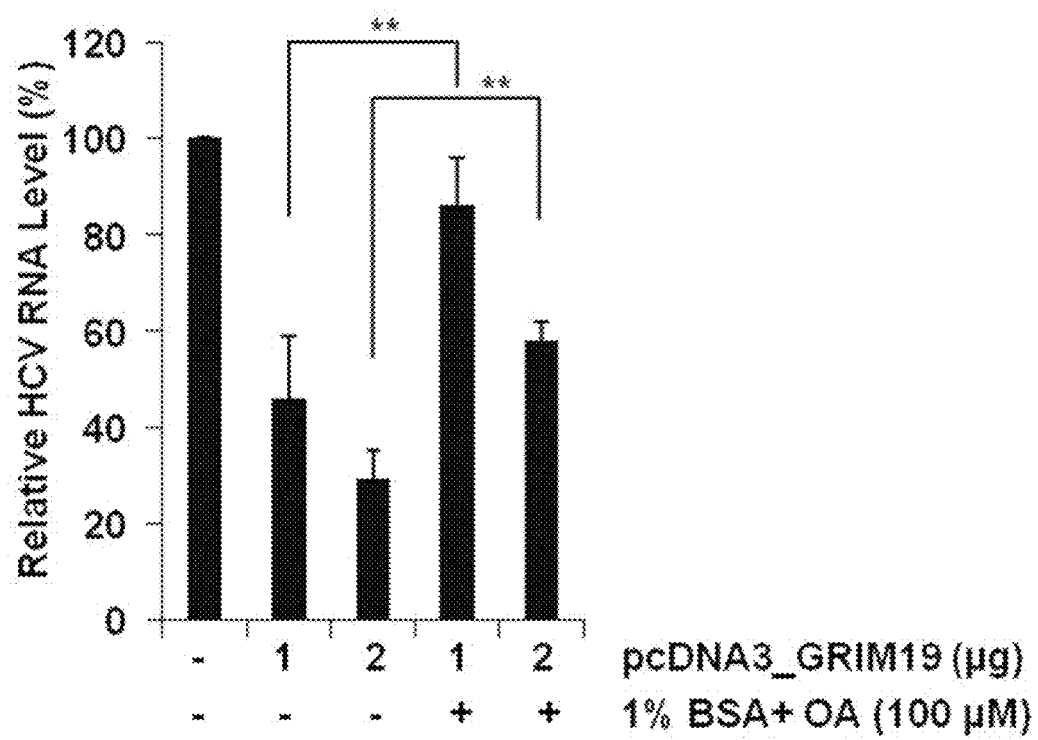
FIG. 6b shows that decreased level of HCV RNA in Huh7 cells due to transfection of a vector expressing GRIM19 to overexpress GRIM19 was restored through treatment with lipid.

Also, with reference to FIG. 6b, it was confirmed that the level of HCV RNA decreased by GRIM19 overexpression due to transfection with pcDNA3_GRIM19 (Example 3) was restored through treatment with oleic acid (OA). From this, it was proved that decrease in the level of HCV RNA by GRIM19 overexpression is associated with lipid accumulation in cells.

EXAMPLE 5

Confirmation of Mechanism of Lipid Decrease in Cells by GRIM19 Overexpression

With reference to Example 6 above, in the case of GRIM19 overexpression due to transfection with pcDNA3_GRIM19, the degree of lipid accumulated in Huh7 cells was decreased. In order to confirm such mechanism, a change in expression of proteins involved in fatty acid synthesis was examined including acetyl-CoA carboxylase (Acc), an enzyme promoting fatty acid synthesis in a fatty acid synthesis process.

After seeding $1.5 \times 10^6$ Huh7 cells in 10-cm culture dish, the cells were cultured using serum free DMEM. After 24 hours, the cells were transfected with pcDNA3_GRIM19, and after 48 hours, the cells were harvested, followed by Western blot analysis. The harvested cells were treated with PRO-PREP™ Protein Extraction Solution of INTRON BIO-TECHNOLOGY, to obtain protein lysates. 30 μg of protein lysates was separated according to size through 8% SDS-PAGE and then transferred to nitrocellulose membrane, and the expression level of ACC was evaluated using ACC specific antibody. As an anti-ACC antibody, a product purchased from Cell Signaling was used. The expression level of protein was visualized through chemiluminescence system (Amersham Pharmacia Biotech). The expression level of ACC was relatively compared by analyzing the density between the visualized ACC proteins bands and loading control β-actin band.

Figure 7A:
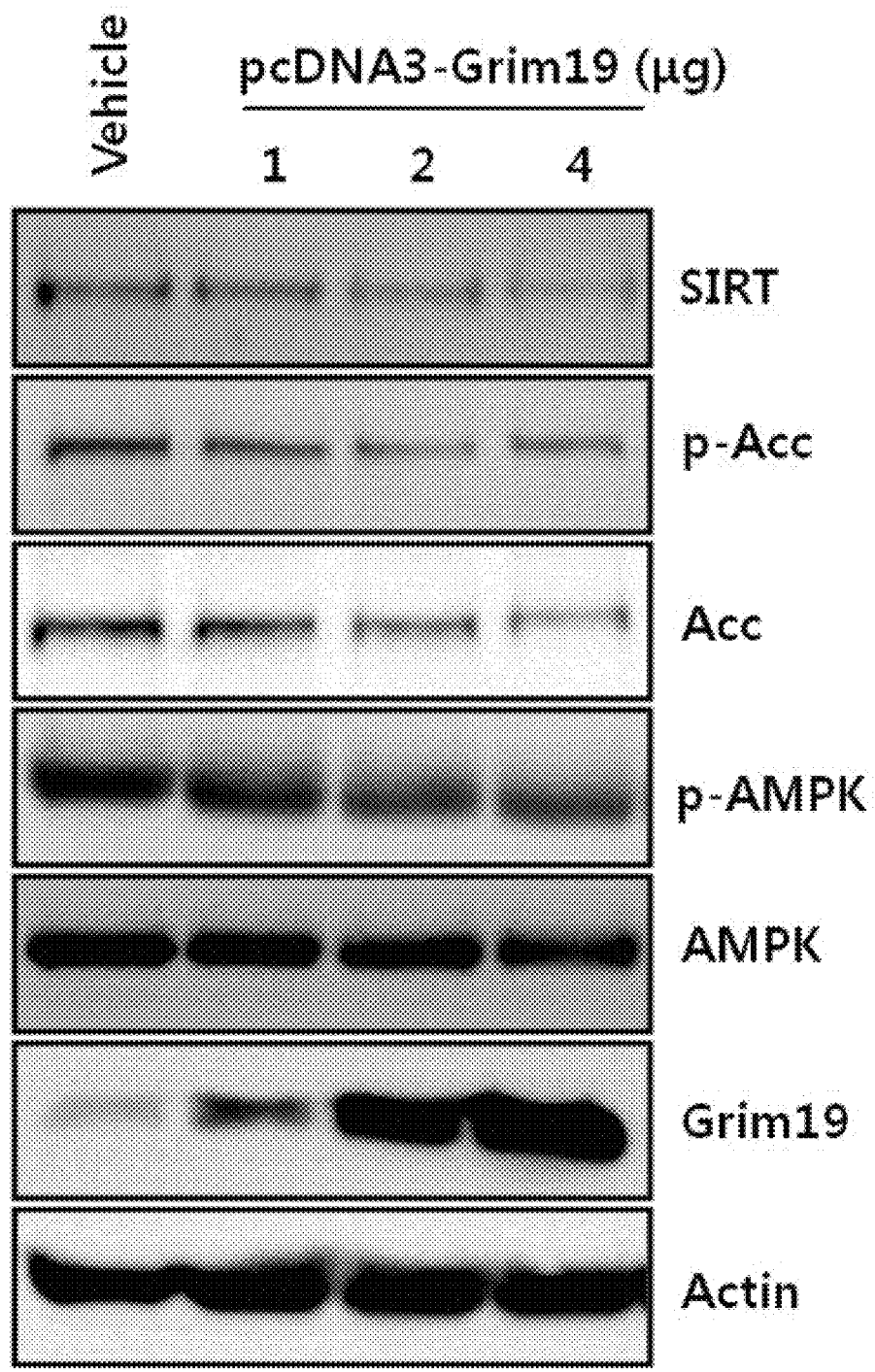
FIG. 7a shows a change in expression of proteins involved in fatty acid synthesis in the case of transfection with pcDNA3_GRIM19 to overexpress GRIM19. "SIRT" indicates sirtuin protein, "p-Acc" indicates phosphor-acetyl-CoA carboxylase, "Acc" indicates acetyl-CoA carboxylase, "p-AMPK" indicates phosphor-AMP-activated protein kinase, "AMPK" indicates AMP-activated protein kinase, and "Actin" indicates actin protein.
Figure 7B:
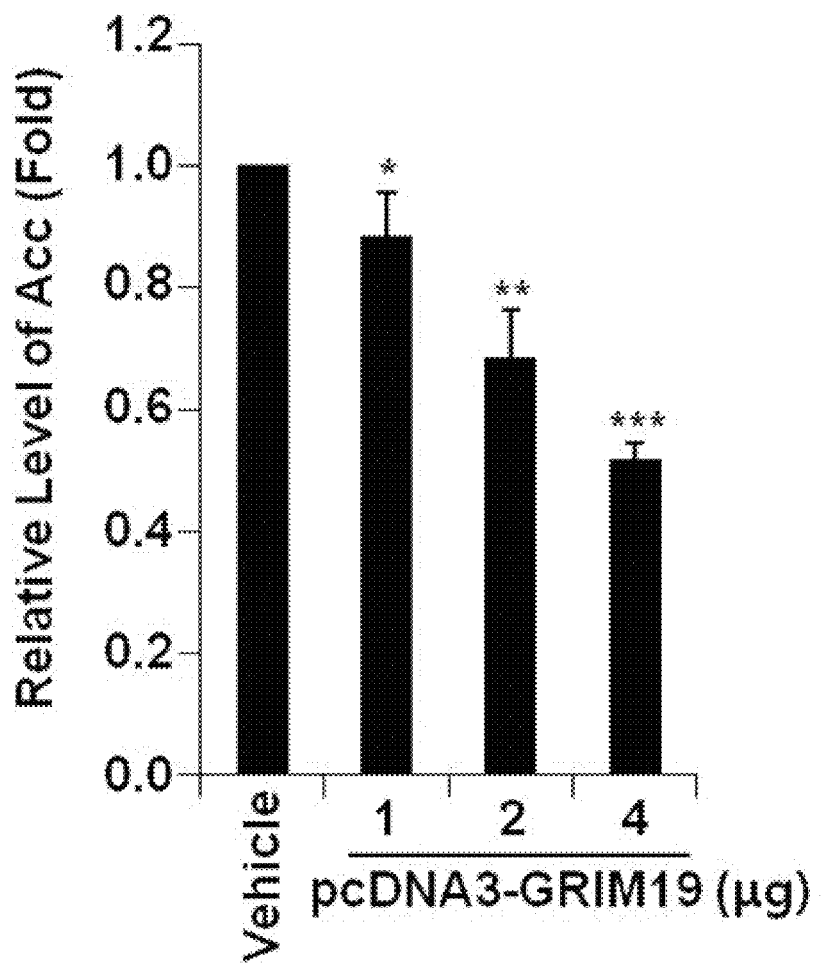
FIG. 7b shows a change in expression of acetyl-CoA carbosylase (Acc) in the case of transfection with pcDNA3_GRIM19 to overexpress GRIM19.

With reference to FIG. 7a and FIG. 7b, it was confirmed that the GRIM19 overexpression due to transfection with pcDNA3_GRIM19 decreases the expression of acetyl-CoA carbosylase.

It was reported that when infected with hepatitis C virus, lipid accumulation in cells was observed, and that in such a case, the activity of SIRT1 is decreased, and accordingly, the activity of AMPK is also decreased, which results in an increase of the activity of ACC and promotion of production of lipid in cells. With reference to FIG. 7a, it was confirmed that the activity of ACC was decreased, whereas the activities of SIRT1 and AMPK were also decreased, which is due to GRIM19 overexpression.

From this, it was proved that the expression level of ACC, among main enzymes involved in lipid metabolism in cells by HCV, is decreased by GRIM19 overexpression, and accordingly, lipid in cells is decreased.

EXAMPLE 6

Synergistic Effect of Inhibiting HCV Through GRIM19 Overexpression and a Combination Treatment of Acc Activity Inhibitor From Example 5 above, it was confirmed that the expression of acetyl-CoA carboxylase (Acc) was decreased when GRIM19 was overexpressed. In this regard, a change in HCV RNA copies was examined in the case of administration of metformin (Sigama Aldrich, Cat. D150959), an activator of AMP-activated protein kinase (AMPK) inhibiting the activity of ACC, in combination.

Figure 8:
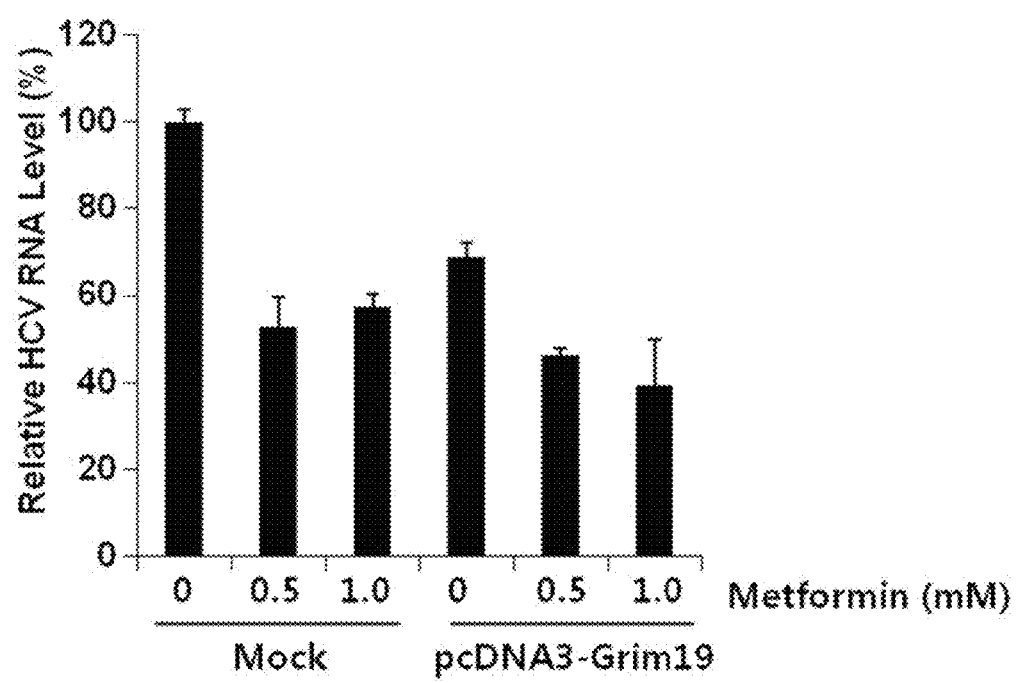
FIG. 8 shows a change in level of HCV RNA in the case of transfection with pcDNA3_GRIM19 to overexpress GRIM19 and treatment with metformin. "Mock" indicates cells with no treatment, and "pcDNA3_GRIM19" indicates the result in cells transfected with a vector expressing GRIM19.

With reference to FIG. 8, the case of transfection with pcDNA3_GRIM19 to overexpress GRIM19 and treatment with metformin leads to a considerably lower increase in HCV RNA than the case of treatment with metformin alone. Thus, it was confirmed that the combination thereof has a synergistic effect of inhibiting HCV.

From this, it was proved that the regulation of fatty acid synthesis including AMPK and Acc protein is involved in the mechanism of decrease in the level of HCV RNA by GRIM19 overexpression.

EXAMPLE 7

Synergistic Effect of Inhibiting HCV Through GRIM19 Overexpression and a Combination Treatment of DGAT-1 Inhibitor As a result of simultaneous treatment of 40 μM of a compound (A922500, MERK) of Formula 1:

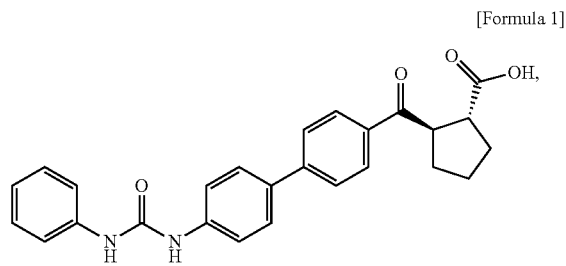 [SMILES: O=C(Nc1ccccc1)Nc1ccc(-c2ccc(C(=O)[C@@H]3CCC[C@H]3C(=O)O)cc2)cc1]

Figure 9:
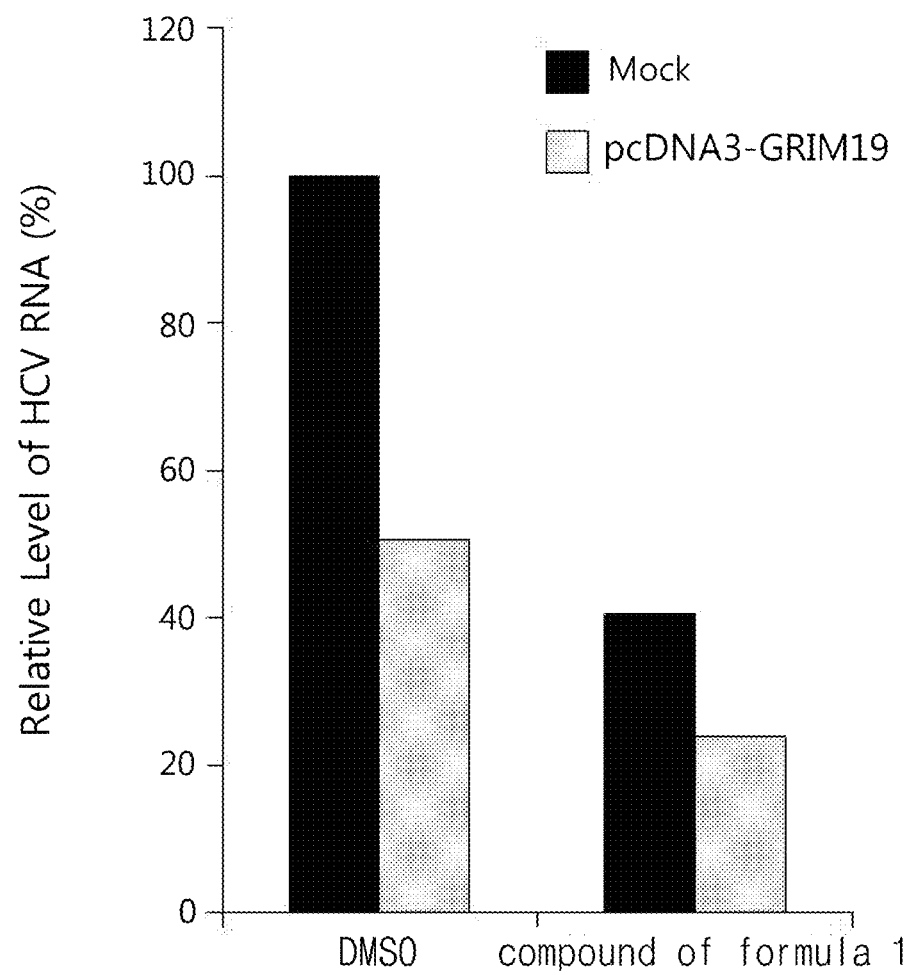
FIG. 9 shows a change in level of HCV RNA in the case of treatment of pcDNA3_GRIM19 transfected cells with a compound (DGAT-1 inhibitor) of Formula 1 in combination. "DMSO" indicates the control group treated with dimethyl sulfoxide (DMSO), instead of the compound of Formula 1, "Mock" indicates cells with no treatment, and "pcDNA3_GRIM19" indicates the result in cells transfected with a vector expressing GRIM19.

[Formula 1]

an inhibitor of DGAT-1, with cells where GRIM19 is overexpressed in HCVcc infected Huh7 cells, based on the fact that HCV replication complex is formed dependent on lipid membrane, and that lipid droplets play an important role in formation of HCV particles, it was confirmed that a synergistic effect of inhibiting HCV replication was shown (FIG. 9).

EXAMPLE 8

Synergistic Effect of Inhibiting HCV Through Treatment of Compound Inhibiting RNA-Dependent RNA Polymerase Activity in In Vitro HCV Infection Model HCVcc infected Huh7 cells were transfected with pcDNA3_GRIM19 using FUGENE HD, as in Example 3 above, the cells were treated with sofosbuvir (Pharma-BLOCK R&D Co. Ltd.) (Formula 2):

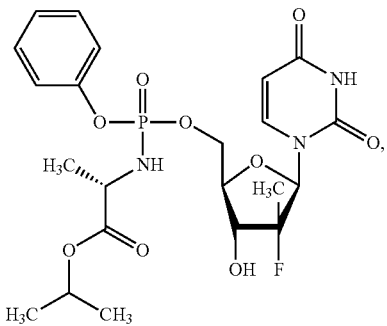

[Formula 2]

a compound inhibiting RNA-dependent RNA polymerase activity of HCV, or the cells were transfected with pcDNA3_GRIM19 and treated with sofosbuvir. Then, a change in HCV RNA copies was evaluated.

Figure 10:
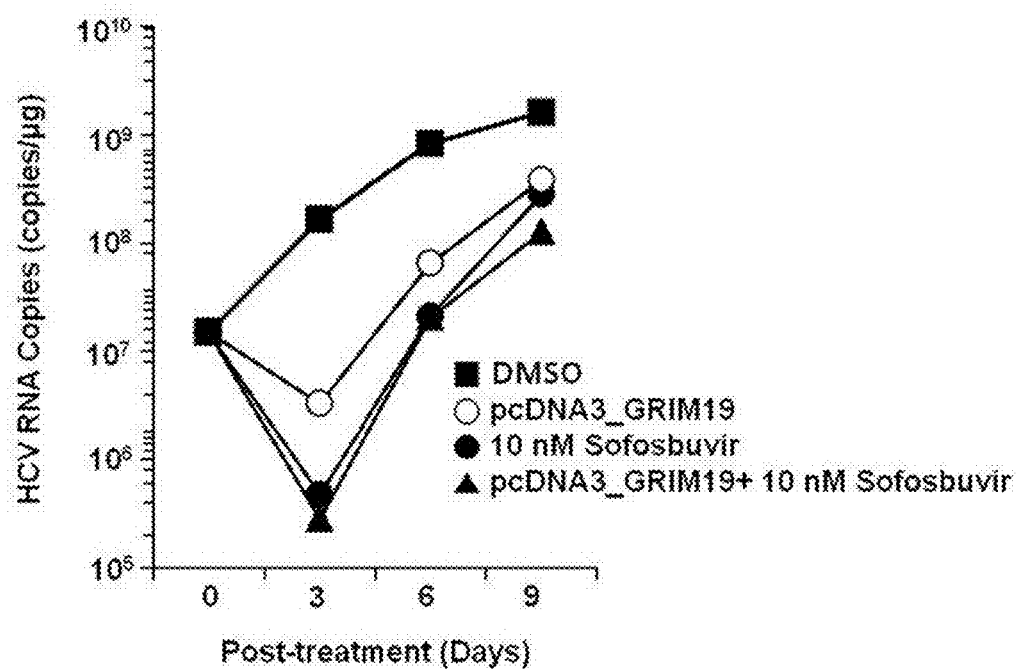
FIG. 10 shows a change in level of HCV RNA in the case of treatment of pcDNA3_GRIM19 transfected cells with a compound (activity inhibitor of RNA-dependent RNA polymerase) of Formula 2. "Sofosbuvir" indicates the compound of Formula 2.

With reference to FIG. 10, it was confirmed that for all the cases excluding the control group treated with dimethyl sulfoxide (DMSO), the level of HCV RNA copies was decreased till $3^{rd}$ day, and then increased again. Further, it was confirmed that the case of transfection with pcDNA3_GRIM19 and treatment with sofosbuvir leads to a lower increase in HCV RNA than the case of treatment with sofosbuvir alone, and thus the combination thereof has a synergistic effect of inhibiting HCV, and that a considerably lower increase of about 45% or more was observed.

EXAMPLE 9

Confirmation of Domains Having Anti-HCV Effect in GRIM19 Protein

Figure 11A:
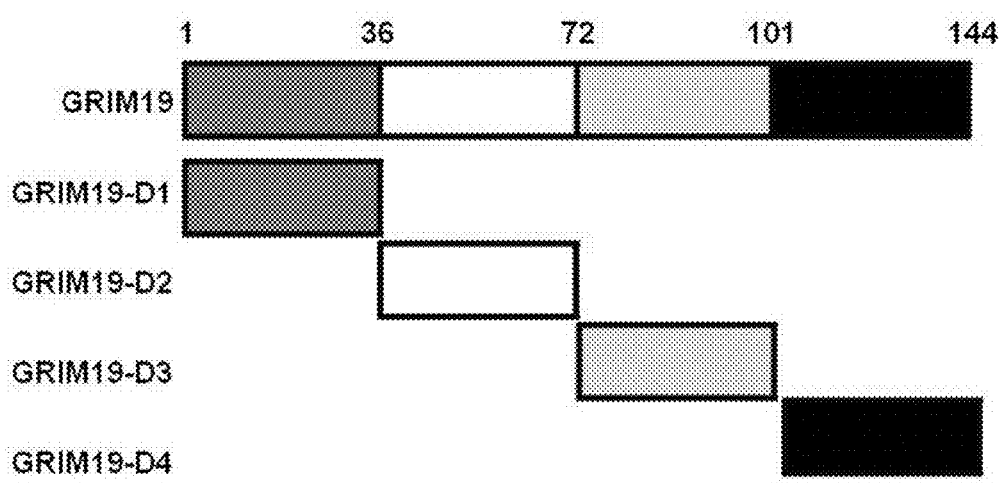
FIG. 11a is a schematic view fragmenting GRIM19 protein into four domains according to the present invention.

GRIM19 protein consists of 144 amino acids. The protein was fragmented into four domains as shown in Table 1 below to confirm domains having anti-HCV effect (FIG. 11a).

TABLE 3

| Domain | Amino acid sequence | Gene sequence (5'→3') |
|---|---|---|
| GRIM19-D1 (aa 1-36) | MAASKVKQDMPPPGG YGPIDYKRNLPRRGLS GYSML (SEQ ID NO: 6) | atggcggcgtcaaaggtgaagcaggacatgcctccgccg gggggctatgggcccatcgactacaaacggaacttgccg cgtcgaggactgtcgggctacagcatgctg (SEQ ID NO: 7) |
| GRIM19-D2 (aa 37-72) | MAIGIGTLIYGHWSIM KWNRERRRLQIEDFEA RIALL (SEQ ID NO: 8) | atggccatagggattggaaccctgatctacgggcactgga gcataatgaagtggaaccgtgagcgcaggcgcctacaaa tcgaggacttcgaggctcgcatcgcgctgttg (SEQ ID NO: 9) |
| GRIM19-D3 (aa 73-101) | MPLLQAETDRRTLQM LRENLEEEAIIMKDV (SEQ ID NO: 10) | atgccactgttacaggcagaaaccgaccggaggaccttg cagatgcttcgggagaacctggaggaggaggccatcatc atgaaggacgtg (SEQ ID NO: 11) |
| GRIM19-D4 (aa 102-144) | MDWKVGESVFHTTRW VPPLIGEL YGLRTTEEA LHASHGFMWYT (SEQ ID NO: 12) | atgcccgactggaaggtgggggagtctgtgttccacacaa cccgctgggtgcccccccttgatcggggagctgtacgggct gcgcaccacagaggaggctctccatgccagccacggctt catgtggtacacg (SEQ ID NO: 13) |

An expression vector which can express the GRIM19-D2 (aa 1-36), GRIM19-D2 (aa 37-72), GRIM19-D3 (aa 73-101), and GRIM19-D4 (aa 102-144) above was prepared, and the effect of each domain was evaluated in in vitro HCV infection model in Example 2.

In order to prepare the expression vector, the gene for each domain of GRIM19 was obtained through PCR with template of the vector expressing pcDNA3_GRIM19, and each domain was subcloned into pCMV-3Tag-3A vector (Agilent Technologies, Inc.) using restriction sites of restriction enzymes EcoRI and SalI. For GRIM19-D2, GRIM19-D3, and GRIM19-D4 to be expressed in the vector, a start codon was added prior to 5' of the actually corresponding gene sequence of GRIM19. Accordingly, for each protein fragment, methionine was added prior to the N terminus of the actually corresponding amino acid sequence of GRIM19.

Figure 11B:
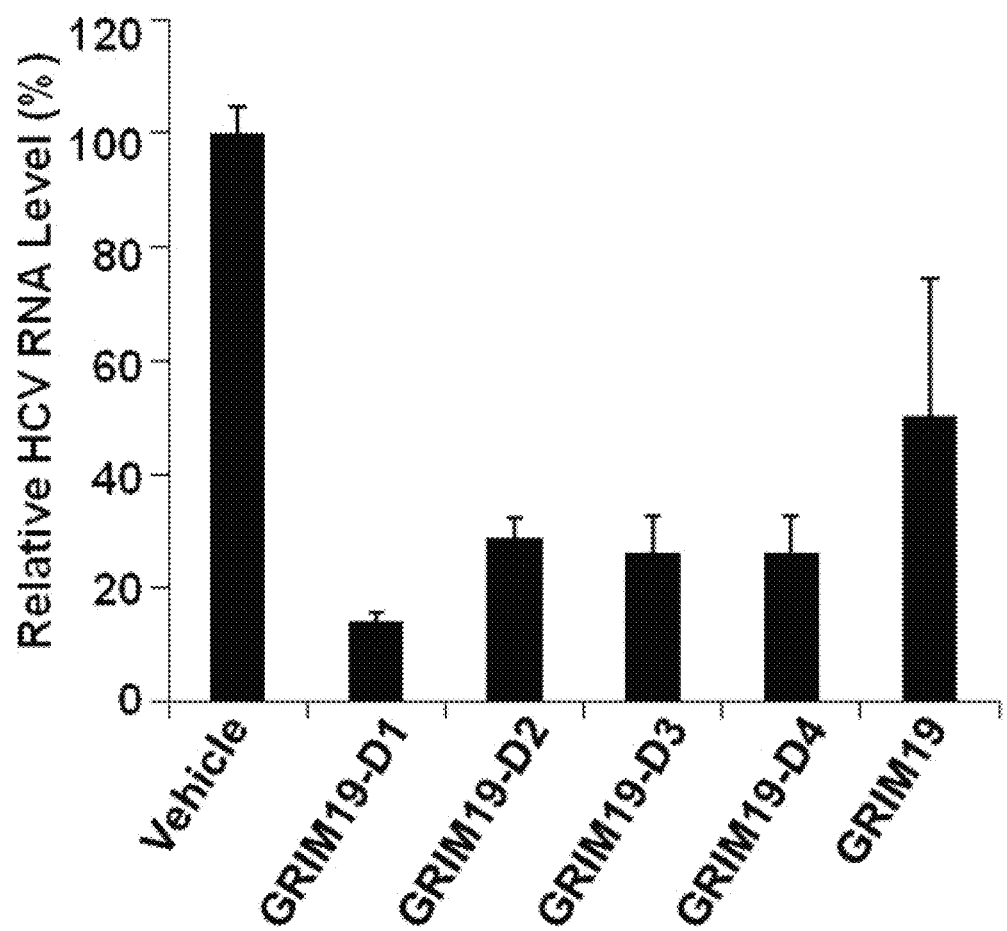
FIG. 11b shows a change in level of HCV RNA in the case of transfection with GRIM19 protein and four domains of GRIM19 protein fragmented according to the present invention in in vitro HCV infection model.

With reference to FIG. 11b, it was confirmed that in the case of overexpression of GRIM19-D1, GRIM19-D2, GRIM19-D3, and GRIM19-D4 domains due to transfection with expression vector that can express each of the prepared domains in in vitro HCV infection model, the level of HCV RNA was significantly decreased in all the domains. Further, it was confirmed that in the case of overexpression of each domain, the level of HCV RNA was significantly decreased, as compared with the case of expression of GRIM19 protein.

Accordingly, it was proved that in the case of the expression of each of four domains of GRIM19, as well as GRIM19 protein, excellent anti-HCV activity was achieved.

EXAMPLE 10

Confirmation of Anti-HCV Effect of Each Domain of GRIM19 Protein

In order to confirm whether an anti-HCV effect is shown when penetrating each domain itself of GRIM19 protein into cells, the effect was evaluated in in vitro HCV infection model by synthesizing peptides in which cell permeable peptide sequences (CP) bind to N-terminal of each domain of GRIM19 of Example 8. The sequences of each domain of GRIM19 comprising the synthesized cell permeable peptide sequences (CP) were analyzed in Table 4 below.

TABLE 4

| | Amino acid sequence |
|---|---|
| CP-GRIM19-D1 | RRRRRRRRRMAASKVKQDMPPPGGYGPIDYKRNL PRRGLSGYSML (SEQ ID NO: 14) |
| CP-GRIM19-D2 | RRRRRRRRRAIGIGTLIYGHWSIMKWNRERRRLQ IEDFEARIALL (SEQ ID NO: 15) |
| CP-GRIM19-D3 | RRRRRRRRRPLLQAETDRRTLQMLRENLEEEAII MKDV (SEQ ID NO: 16) |

After treating Huh7 cells infected with HCVcc through in vitro HCV infection model of Example 2 with 10 μM of CP-GRIM19-D1, CP-GRIM19-D2, and CP-GRIM19-D3 for 48 hours, the level of RNA in HCV was examined.

Figure 12:
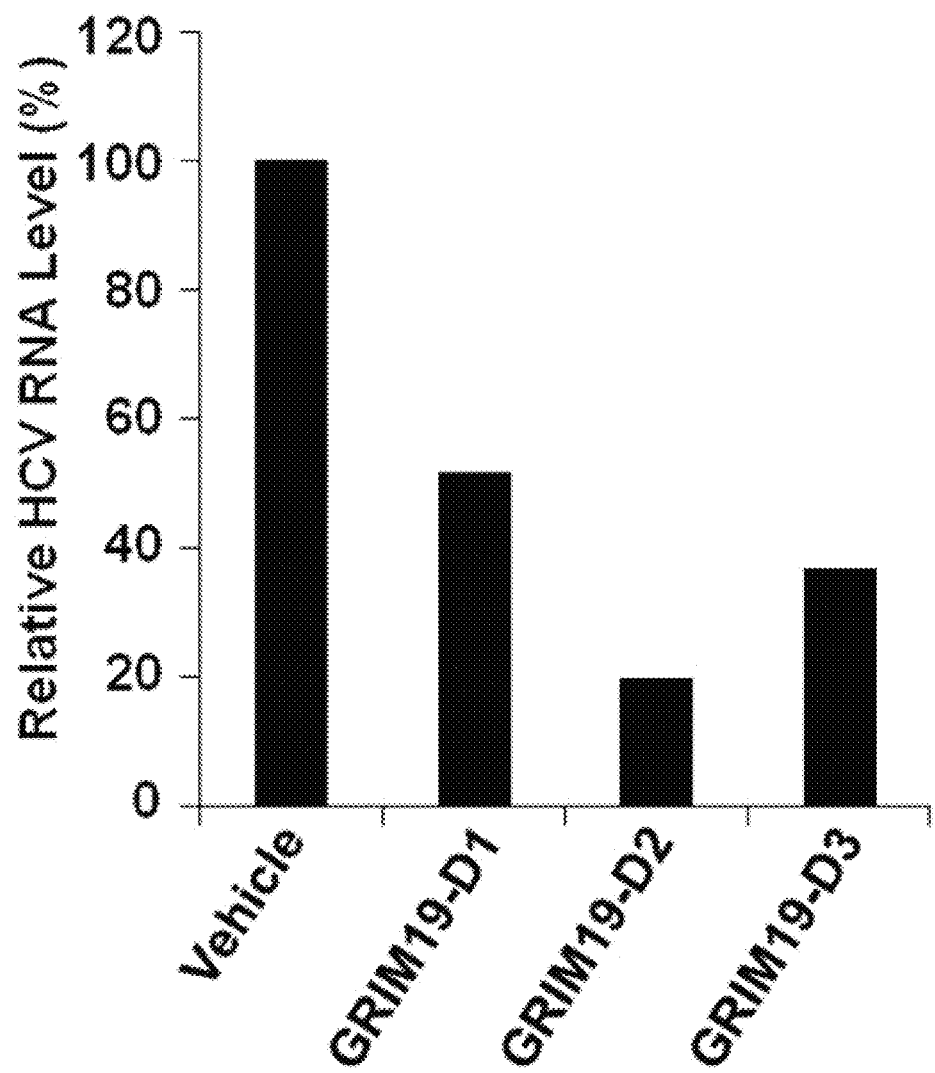
FIG. 12 shows a change in level of HCV RNA in the case of direct treatment of in vitro HCV infection model with peptides where cell permeable peptide sequences (CP) bind to four domains of GRIM19 protein fragmented according to the present invention.

With reference to FIG. 12, it was confirmed that the level of HCV RNA was significantly decreased in HCV infected cells when treating the cells with CP-GRIM19-D1, CP-GRIM19-D2, and CP-GRIM19-D3.

Therefore, it was proved that in addition to the case of transfection with GRIM19 protein or domains of GRIM19 protein and expression of them directly in cells, in the case of treatment with GRIM19 protein or domains of GRIM19 protein directly out of cells, an excellent anti-HCV effect is achieved.

The present invention was conducted by the following research and development program support.

1) Support institute: Korea Seoul St. Mary's Hospital
2) Project: Preparation of corresponding project such as clinics research funds, excellent researcher's project
3) Task: Research on inhibition of hepatitis C virus replication using STAT3 activity inhibitor
4) Chief of research: YOON, Seung Kew
5) Research period: Nov. 1, 2013 to Oct. 31, 2014

INDUSTRIAL AVAILABILITY

The pharmaceutical composition for preventing or treating a hepatitis C virus infectious disease or the antiviral composition against hepatitis C virus of the present invention, comprising GRIM19 protein or a fragment thereof, and a gene encoding the protein or the fragment thereof, can treat patients on whom the standard-of-care treatment for hepatitis C virus does not work, and treat or prevent a hepatitis C virus infectious diseases by inhibiting replication of hepatitis C virus, irrespective of genotype, thereby being useable in the field of treatment of hepatitis C.

What is claimed is:

1. A method for treating a hepatitis C virus infectious disease, the method comprising:
   selecting a subject in need of treatment for a hepatitis C virus infectious disease; and
   administering to the subject a therapeutically effective amount of a pharmaceutical composition comprising at least one selected from the group consisting of genes-associated with Retinoid-Interferon induced Morality 19 (GRIM19) protein or a fragment thereof, or a gene encoding the GRIM19 protein or the fragment thereof,
   wherein the GRIM19 protein consists of the amino acid sequence of SEQ ID NO: 2,
   wherein the gene encoding the GRIM19 protein consists of the base sequence of SEQ ID NO: 1, and
   wherein the fragment of GRIM19 protein is at least one selected from the group consisting of:
   a protein fragment comprising $1^{st}$ to $36^{th}$ amino acids of the amino acid sequence of SEQ ID NO: 2;
   a protein fragment comprising $37^{th}$ to $72^{nd}$ amino acids of the amino acid sequence of SEQ ID NO: 2;
   a protein fragment comprising $73^{rd}$ to $101^{st}$ amino acids of the amino acid sequence of SEQ ID NO: 2; and
   a protein fragment comprising $102^{nd}$ to $144^{th}$ amino acids of the amino acid sequence of SEQ ID NO: 2.

2. The method of claim 1, wherein the fragment of GRIM19 protein consists of the amino acid sequence selected from the group consisting of SEQ ID NO: 6, SEQ ID NO: 8, SEQ ID NO: 10, and SEQ ID NO: 12.

3. The method of claim 1, wherein the gene encoding the fragment of GRIM19 protein is at least one selected from the group consisting of:
   a gene comprising $3^{rd}$ to $108^{th}$ bases of the base sequence of SEQ ID NO: 1;
   a gene comprising $109^{th}$ to $216^{th}$ bases of the base sequence of SEQ ID NO: 1;
   a gene comprising $217^{th}$ to $303^{rd}$ bases of the base sequence of SEQ ID NO: 1; and
   a gene comprising $304^{th}$ to $432^{nd}$ bases of the base sequence of SEQ ID NO: 1.

4. The method of claim 1, wherein the gene encoding the fragment of GRIM19 protein consists of the base sequence selected from the group consisting of SEQ ID NO: 7, SEQ ID NO: 9, SEQ ID NO: 11, and SEQ ID NO: 13.

5. The method of claim 1, wherein the GRIM19 protein or the fragment thereof further comprises a cell penetrating peptide at an N-terminus, C-terminus, or both termini.

6. The method of claim 5, wherein the cell penetrating peptide consists of the amino acid sequence selected from the group consisting of SEQ ID NO: 19, SEQ ID NO: 20, SEQ ID NO: 21, and SEQ ID NO: 22.

7. The method of claim 1, wherein the gene encoding the GRIM19protein or the fragment thereof is provided in a form included in a recombinant vector.

8. The method of claim 1, wherein the composition further comprises a substance inhibiting expression or activity of diacylglycerol acyltransferase-1 (DGAT-1).

9. The method of claim 8, wherein the substance inhibiting the expression or activity of DGAT-1 is siRNA, shRNA, or antisense oligonucleotide, specifically binding to the gene or mRNA of DGAT-1.

10. The method of claim 8, wherein the substance inhibiting the expression or activity of DGAT-1 is an antibody, an aptamer, or a compound of Formula 1:

[Formula 1]

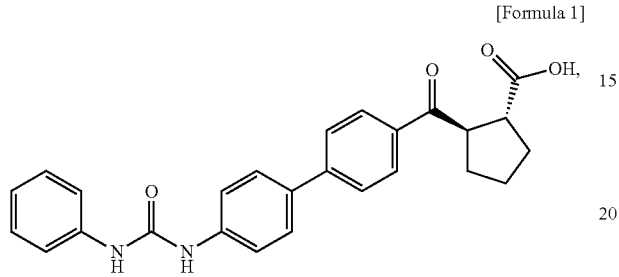

or a salt thereof, specifically binding to DGAT-1.

11. The method of claim 1, wherein the composition further comprises a substance inhibiting expression or activity of RNA-dependent RNA polymerase.

12. The method of claim 11, wherein the substance inhibiting the expression or activity of RNA-dependent RNA polymerase is a compound of Formula 2:

[Formula 2]

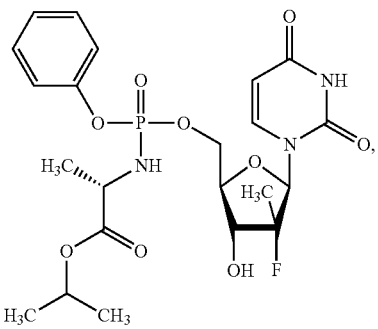

or a salt thereof.

13. The method of claim 1, wherein the composition further comprises a substance activating AMP-activated protein kinase (AMPK).

14. The method of claim 13, wherein the substance activating AMP-activated protein kinase (AMPK) is metformin.

15. The method of claim 1, wherein the hepatitis C virus infectious disease is at least one of hepatitis C, liver fibrosis caused by hepatitis C virus, liver cirrhosis caused by hepatitis C virus, and liver cancer caused by hepatitis C virus.

\* \* \* \* \*

SEQUENCE LISTING

```
<160> NUMBER OF SEQ ID NOS: 22

<210> SEQ ID NO 1
<211> LENGTH: 435
<212> TYPE: DNA
<213> ORGANISM: Homo sapiens
<220> FEATURE:
<221> NAME/KEY: gene
<222> LOCATION: (1)..(435)
<223> OTHER INFORMATION: GRIM 19 gene

<400> SEQUENCE: 1
atggcggcgt caaaggtgaa gcaggacatg cctccgccgg ggggctatgg gcccatcgac      60
tacaaacgga acttgccgcg tcgaggactg tcgggctaca gcatgctggc catagggatt     120
ggaaccctga tctacgggca ctggagcata atgaagtgga accgtgagcg caggcgccta     180
caaatcgagg acttcgaggc tcgcatcgcg ctgttgccac tgttacaggc agaaaccgac     240
cggaggacct tgcagatgct tcgggagaac ctggaggagg aggccatcat catgaaggac     300
gtgcccgact ggaaggtggg ggagtctgtg ttccacacaa cccgctgggt gccccccttg     360
atcggggagc tgtacgggct gcgcaccaca gaggaggctc tccatgccag ccacggcttc     420
atgtggtaca cgtag                                                     435

<210> SEQ ID NO 2
<211> LENGTH: 144
<212> TYPE: PRT
<213> ORGANISM: Homo sapiens
```

-continued

```
<220> FEATURE:
<221> NAME/KEY: PEPTIDE
<222> LOCATION: (1)..(144)
<223> OTHER INFORMATION: GRIM19 peptide

<400> SEQUENCE: 2

Met Ala Ala Ser Lys Val Lys Gln Asp Met Pro Pro Gly Gly Tyr
 1               5                  10                  15

Gly Pro Ile Asp Tyr Lys Arg Asn Leu Pro Arg Arg Gly Leu Ser Gly
                20                  25                  30

Tyr Ser Met Leu Ala Ile Gly Ile Gly Thr Leu Ile Tyr Gly His Trp
            35                  40                  45

Ser Ile Met Lys Trp Asn Arg Glu Arg Arg Leu Gln Ile Glu Asp
        50                  55                  60

Phe Glu Ala Arg Ile Ala Leu Leu Pro Leu Leu Gln Ala Glu Thr Asp
 65                 70                  75                  80

Arg Arg Thr Leu Gln Met Leu Arg Glu Asn Leu Glu Glu Glu Ala Ile
                85                  90                  95

Ile Met Lys Asp Val Pro Asp Trp Lys Val Gly Glu Ser Val Phe His
            100                 105                 110

Thr Thr Arg Trp Val Pro Pro Leu Ile Gly Glu Leu Tyr Gly Leu Arg
        115                 120                 125

Thr Thr Glu Glu Ala Leu His Ala Ser His Gly Phe Met Trp Tyr Thr
130                 135                 140

<210> SEQ ID NO 3
<211> LENGTH: 21
<212> TYPE: DNA
<213> ORGANISM: Artificial Sequence
<220> FEATURE:
<223> OTHER INFORMATION: HCV 5' UTR probe

<400> SEQUENCE: 3
ctgcggaacc ggtgagtaca c                                            21

<210> SEQ ID NO 4
<211> LENGTH: 30
<212> TYPE: DNA
<213> ORGANISM: Artificial Sequence
<220> FEATURE:
<223> OTHER INFORMATION: HCV 5'UTR Forward Primer

<400> SEQUENCE: 4
gcgcctagcc atggcgttag tatgagtgtc                                   30

<210> SEQ ID NO 5
<211> LENGTH: 30
<212> TYPE: DNA
<213> ORGANISM: Artificial Sequence
<220> FEATURE:
<223> OTHER INFORMATION: HCV 5'UTR Reverse Primer

<400> SEQUENCE: 5
accacaaggc ctttcgcaac ccaacgctac                                   30

<210> SEQ ID NO 6
<211> LENGTH: 36
<212> TYPE: PRT
<213> ORGANISM: Artificial Sequence
<220> FEATURE:
<223> OTHER INFORMATION: GRIM19-D1
```

```
<220> FEATURE:
<221> NAME/KEY: PEPTIDE
<222> LOCATION: (1)..(36)
<223> OTHER INFORMATION: Fragment of GRIM19 (comprising amino acid from
      1st to 36th of GRIM19 protein)

<400> SEQUENCE: 6

Met Ala Ala Ser Lys Val Lys Gln Asp Met Pro Pro Gly Gly Tyr
1               5                   10                  15

Gly Pro Ile Asp Tyr Lys Arg Asn Leu Pro Arg Arg Gly Leu Ser Gly
            20                  25                  30

Tyr Ser Met Leu
        35

<210> SEQ ID NO 7
<211> LENGTH: 108
<212> TYPE: DNA
<213> ORGANISM: Artificial Sequence
<220> FEATURE:
<223> OTHER INFORMATION: GRIM19-D1 gene
<220> FEATURE:
<221> NAME/KEY: gene
<222> LOCATION: (1)..(108)
<223> OTHER INFORMATION: GRIM19-D1 coding gene

<400> SEQUENCE: 7
atggcggcgt caaaggtgaa gcaggacatg cctccgccgg ggggctatgg gcccatcgac      60
tacaaacgga acttgccgcg tcgaggactg tcgggctaca gcatgctg                 108

<210> SEQ ID NO 8
<211> LENGTH: 37
<212> TYPE: PRT
<213> ORGANISM: Artificial Sequence
<220> FEATURE:
<223> OTHER INFORMATION: GRIM19-D2
<220> FEATURE:
<221> NAME/KEY: PEPTIDE
<222> LOCATION: (1)..(37)
<223> OTHER INFORMATION: Fragment of GRIM19 (comprising amino acid from
      37th to 72nd of GRIM19 protein)

<400> SEQUENCE: 8

Met Ala Ile Gly Ile Gly Thr Leu Ile Tyr Gly His Trp Ser Ile Met
1               5                   10                  15

Lys Trp Asn Arg Glu Arg Arg Arg Leu Gln Ile Glu Asp Phe Glu Ala
            20                  25                  30

Arg Ile Ala Leu Leu
        35

<210> SEQ ID NO 9
<211> LENGTH: 111
<212> TYPE: DNA
<213> ORGANISM: Artificial Sequence
<220> FEATURE:
<223> OTHER INFORMATION: GRIM19-D2 gene

<400> SEQUENCE: 9
atggccatag ggattggaac cctgatctac gggcactgga gcataatgaa gtggaaccgt      60
gagcgcaggc gcctacaaat cgaggacttc gaggctcgca tcgcgctgtt g              111

<210> SEQ ID NO 10
<211> LENGTH: 30
<212> TYPE: PRT
<213> ORGANISM: Artificial Sequence
```

```
<220> FEATURE:
<223> OTHER INFORMATION: GRIM19-D3
<220> FEATURE:
<221> NAME/KEY: PEPTIDE
<222> LOCATION: (1)..(30)
<223> OTHER INFORMATION: Fragment of GRIM19 (comprising amino acid from
      73rd to 101st of GRIM19 protein)

<400> SEQUENCE: 10

Met Pro Leu Leu Gln Ala Glu Thr Asp Arg Arg Thr Leu Gln Met Leu
 1               5                  10                  15

Arg Glu Asn Leu Glu Glu Glu Ala Ile Ile Met Lys Asp Val
             20                  25                  30

<210> SEQ ID NO 11
<211> LENGTH: 90
<212> TYPE: DNA
<213> ORGANISM: Artificial Sequence
<220> FEATURE:
<223> OTHER INFORMATION: GRIM19-D3

<400> SEQUENCE: 11
atgccactgt tacaggcaga aaccgaccgg aggaccttgc agatgcttcg ggagaacctg      60
gaggaggagg ccatcatcat gaaggacgtg                                      90

<210> SEQ ID NO 12
<211> LENGTH: 43
<212> TYPE: PRT
<213> ORGANISM: Artificial Sequence
<220> FEATURE:
<223> OTHER INFORMATION: GRIM19-D4
<220> FEATURE:
<221> NAME/KEY: PEPTIDE
<222> LOCATION: (1)..(43)
<223> OTHER INFORMATION: Fragment of GRIM19 (comprising amino acid from
      102nd to 144th of GRIM19 protein)

<400> SEQUENCE: 12

Met Asp Trp Lys Val Gly Glu Ser Val Phe His Thr Thr Arg Trp Val
 1               5                  10                  15

Pro Pro Leu Ile Gly Glu Leu Tyr Gly Leu Arg Thr Thr Glu Glu Ala
             20                  25                  30

Leu His Ala Ser His Gly Phe Met Trp Tyr Thr
         35                  40

<210> SEQ ID NO 13
<211> LENGTH: 132
<212> TYPE: DNA
<213> ORGANISM: Artificial Sequence
<220> FEATURE:
<223> OTHER INFORMATION: GRIM19-D4 gene

<400> SEQUENCE: 13
atgcccgact ggaaggtggg ggagtctgtg ttccacacaa cccgctgggt gcccccttg       60 atcggggagc tgtacgggct gcgcaccaca gaggaggctc tccatgccag ccacggcttc    120
atgtggtaca cg                                                        132

<210> SEQ ID NO 14
<211> LENGTH: 45
<212> TYPE: PRT
<213> ORGANISM: Artificial Sequence
<220> FEATURE:
<223> OTHER INFORMATION: CP-GRIM19-D1
```

```
<400> SEQUENCE: 14

Arg Arg Arg Arg Arg Arg Arg Arg Met Ala Ala Ser Lys Val Lys
 1               5                  10                  15

Gln Asp Met Pro Pro Gly Gly Tyr Gly Pro Ile Asp Tyr Lys Arg
                20                  25                  30

Asn Leu Pro Arg Arg Gly Leu Ser Gly Tyr Ser Met Leu
            35                  40                  45

<210> SEQ ID NO 15
<211> LENGTH: 45
<212> TYPE: PRT
<213> ORGANISM: Artificial Sequence
<220> FEATURE:
<223> OTHER INFORMATION: CP-GRIM19-D2

<400> SEQUENCE: 15

Arg Arg Arg Arg Arg Arg Arg Arg Arg Ala Ile Gly Ile Gly Thr Leu
 1               5                  10                  15

Ile Tyr Gly His Trp Ser Ile Met Lys Trp Asn Arg Glu Arg Arg
                20                  25                  30

Leu Gln Ile Glu Asp Phe Glu Ala Arg Ile Ala Leu Leu
            35                  40                  45

<210> SEQ ID NO 16
<211> LENGTH: 38
<212> TYPE: PRT
<213> ORGANISM: Artificial Sequence
<220> FEATURE:
<223> OTHER INFORMATION: CP-GRIM19-D3

<400> SEQUENCE: 16

Arg Arg Arg Arg Arg Arg Arg Arg Arg Pro Leu Leu Gln Ala Glu Thr
 1               5                  10                  15

Asp Arg Arg Thr Leu Gln Met Leu Arg Glu Asn Leu Glu Glu Glu Ala
                20                  25                  30

Ile Ile Met Lys Asp Val
            35

<210> SEQ ID NO 17
<211> LENGTH: 1467
<212> TYPE: DNA
<213> ORGANISM: Homo sapiens
<220> FEATURE:
<221> NAME/KEY: gene
<222> LOCATION: (1)..(1467)
<223> OTHER INFORMATION: DGAT-1 gene

<400> SEQUENCE: 17
atgggcgacc gcggcagctc ccggcgccgg aggacagggt cgcggccctc gagccacggc    60
ggcggcgggc ctgcgcggc ggaagaggag gtgcgggacg ccgctgcggg ccccgacgtg   120
ggagccgcgg gggacgcgcc agccccggcc cccaacaagg acgagacgc cggcgtgggc   180 agcggccact gggagctgag gtgccatcgc ctgcaggatt ctttattcag ctctgacagt   240
ggcttcagca actaccgtgg catcctgaac tggtgtgtgg tgatgctgat cttgagcaat   300
gcccggttat ttctggagaa cctcatcaag tatggcatcc tggtgaccc catccaggtg   360 gtttctctgt tcctgaagga tccctatagc tggcccgccc catgcctggt tattgcggcc   420
aatgtctttg ctgtggctgc attccaggtt gagaagcgcc tggcggtggg tgccctgacg   480
gagcaggcgg gactgctgct gcacgtggcc aacctggcca ccattctgtg tttcccagcg   540
```

```
gctgtggtct tactggttga gtctatcact ccagtgggct ccctgctggc gctgatggcg      600
cacaccatcc tcttcctcaa gctcttctcc taccgcgacg tcaactcatg gtgccgcagg      660
gccagggcca aggctgcctc tgcagggaag aaggccagca gtgctgctgc cccgcacacc      720
gtgagctacc cggacaatct gacctaccgc gatctctact acttcctctt cgcccccacc      780
ttgtgctacg agctcaactt tccccgctct ccccgcatcc ggaagcgctt tctgctgcga      840
cggatccttg agatgctgtt cttcacccag ctccaggtgg ggctgatcca gcagtggatg      900
gtccccacca tccagaactc catgaagccc ttcaaggaca tggactactc acgcatcatc      960
gagcgcctcc tgaagctggc ggtccccaat cacctcatct ggctcatctt cttctactgg     1020
ctcttccact cctgcctgaa tgccgtggct gagctcatgc agtttggaga ccgggagttc     1080
taccgggact ggtggaactc cgagtctgtc acctacttct ggcagaactg gaacatccct     1140
gtgcacaagt ggtgcatcag acacttctac aagcccatgc ttcgacgggg cagcagcaag     1200
tggatggcca ggacaggggt gttcctggcc tcggccttct tccacgagta cctggtgagc     1260
gtccctctgc gaatgttccg cctctgggcg ttcacgggca tgatggctca gatcccactg     1320
gcctggttcg tgggccgctt tttccagggc aactatggca cgcagctgt gtggctgtcg     1380 ctcatcatcg gacagccaat agccgtcctc atgtacgtcc acgactacta cgtgctcaac     1440
tatgaggccc cagcggcaga ggcctga                                         1467
```

```
<210> SEQ ID NO 18
<211> LENGTH: 488
<212> TYPE: PRT
<213> ORGANISM: Homo sapiens
<220> FEATURE:
<221> NAME/KEY: PEPTIDE
<222> LOCATION: (1)..(488)
<223> OTHER INFORMATION: DGAT-1 peptide

<400> SEQUENCE: 18

Met Gly Asp Arg Gly Ser Ser Arg Arg Arg Thr Gly Ser Arg Pro
 1               5                  10                  15

Ser Ser His Gly Gly Gly Gly Pro Ala Ala Ala Glu Glu Val Arg
                20                  25                  30

Asp Ala Ala Ala Gly Pro Asp Val Gly Ala Ala Gly Asp Ala Pro Ala
            35                  40                  45

Pro Ala Pro Asn Lys Asp Gly Asp Ala Gly Val Gly Ser Gly His Trp
        50                  55                  60

Glu Leu Arg Cys His Arg Leu Gln Asp Ser Leu Phe Ser Ser Asp Ser
    65                  70                  75                  80

Gly Phe Ser Asn Tyr Arg Gly Ile Leu Asn Trp Cys Val Val Met Leu
                85                  90                  95

Ile Leu Ser Asn Ala Arg Leu Phe Leu Glu Asn Leu Ile Lys Tyr Gly
            100                 105                 110

Ile Leu Val Asp Pro Ile Gln Val Val Ser Leu Phe Leu Lys Asp Pro
        115                 120                 125

Tyr Ser Trp Pro Ala Pro Cys Leu Val Ile Ala Ala Asn Val Phe Ala
    130                 135                 140

Val Ala Ala Phe Gln Val Glu Lys Arg Leu Ala Val Gly Ala Leu Thr
145                 150                 155                 160

Glu Gln Ala Gly Leu Leu Leu His Val Ala Asn Leu Ala Thr Ile Leu
                165                 170                 175

Cys Phe Pro Ala Ala Val Val Leu Leu Val Glu Ser Ile Thr Pro Val
            180                 185                 190
```

```
Gly Ser Leu Leu Ala Leu Met Ala His Thr Ile Leu Phe Leu Lys Leu
            195                 200                 205
Phe Ser Tyr Arg Asp Val Asn Ser Trp Cys Arg Ala Arg Ala Lys
210                 215                 220
Ala Ala Ser Ala Gly Lys Lys Ala Ser Ser Ala Ala Pro His Thr
225                 230                 235                 240
Val Ser Tyr Pro Asp Asn Leu Thr Tyr Arg Asp Leu Tyr Tyr Phe Leu
            245                 250                 255
Phe Ala Pro Thr Leu Cys Tyr Glu Leu Asn Phe Pro Arg Ser Pro Arg
            260                 265                 270
Ile Arg Lys Arg Phe Leu Leu Arg Arg Ile Leu Glu Met Leu Phe Phe
            275                 280                 285
Thr Gln Leu Gln Val Gly Leu Ile Gln Gln Trp Met Val Pro Thr Ile
            290                 295                 300
Gln Asn Ser Met Lys Pro Phe Lys Asp Met Asp Tyr Ser Arg Ile Ile
305                 310                 315                 320
Glu Arg Leu Leu Lys Leu Ala Val Pro Asn His Leu Ile Trp Leu Ile
                325                 330                 335
Phe Phe Tyr Trp Leu Phe His Ser Cys Leu Asn Ala Val Ala Glu Leu
            340                 345                 350
Met Gln Phe Gly Asp Arg Glu Phe Tyr Arg Asp Trp Asn Ser Glu
            355                 360                 365
Ser Val Thr Tyr Phe Trp Gln Asn Trp Asn Ile Pro Val His Lys Trp
            370                 375                 380
Cys Ile Arg His Phe Tyr Lys Pro Met Leu Arg Arg Gly Ser Ser Lys
385                 390                 395                 400
Trp Met Ala Arg Thr Gly Val Phe Leu Ala Ser Ala Phe Phe His Glu
                405                 410                 415
Tyr Leu Val Ser Val Pro Leu Arg Met Phe Arg Leu Trp Ala Phe Thr
            420                 425                 430
Gly Met Met Ala Gln Ile Pro Leu Ala Trp Phe Val Gly Arg Phe Phe
            435                 440                 445
Gln Gly Asn Tyr Gly Asn Ala Ala Val Trp Leu Ser Leu Ile Ile Gly
450                 455                 460
Gln Pro Ile Ala Val Leu Met Tyr Val His Asp Tyr Tyr Val Leu Asn
465                 470                 475                 480
Tyr Glu Ala Pro Ala Ala Glu Ala
            485

<210> SEQ ID NO 19
<211> LENGTH: 9
<212> TYPE: PRT
<213> ORGANISM: Artificial Sequence
<220> FEATURE:
<223> OTHER INFORMATION: R9 peptide
<220> FEATURE:
<221> NAME/KEY: PEPTIDE
<222> LOCATION: (1)..(9)
<223> OTHER INFORMATION: Cell Penetrating Peptide

<400> SEQUENCE: 19

Arg Arg Arg Arg Arg Arg Arg Arg Arg
  1               5

<210> SEQ ID NO 20
<211> LENGTH: 16
<212> TYPE: PRT
<213> ORGANISM: Artificial Sequence
```

```
<220> FEATURE:
<223> OTHER INFORMATION: Penetratin peptide
<220> FEATURE:
<221> NAME/KEY: PEPTIDE
<222> LOCATION: (1)..(16)
<223> OTHER INFORMATION: Cell Penetrating Peptide

<400> SEQUENCE: 20

Arg Gln Ile Lys Ile Trp Phe Gln Asn Arg Arg Met Lys Trp Lys Lys
 1               5                   10                  15

<210> SEQ ID NO 21
<211> LENGTH: 13
<212> TYPE: PRT
<213> ORGANISM: Artificial Sequence
<220> FEATURE:
<223> OTHER INFORMATION: TAT peptide
<220> FEATURE:
<221> NAME/KEY: PEPTIDE
<222> LOCATION: (1)..(13)
<223> OTHER INFORMATION: Cell Penetrating Peptide

<400> SEQUENCE: 21

Gly Arg Lys Lys Arg Arg Gln Arg Arg Arg Pro Pro Gln
 1               5                   10

<210> SEQ ID NO 22
<211> LENGTH: 16
<212> TYPE: PRT
<213> ORGANISM: Artificial Sequence
<220> FEATURE:
<223> OTHER INFORMATION: MTS peptide
<220> FEATURE:
<221> NAME/KEY: PEPTIDE
<222> LOCATION: (1)..(16)
<223> OTHER INFORMATION: Cell Penetrating Peptide

<400> SEQUENCE: 22

Ala Ala Val Ala Leu Leu Pro Ala Val Leu Leu Ala Leu Leu Ala Pro
 1               5                   10                  15
```